(12) United States Patent
Riley et al.

(10) Patent No.: US 7,670,781 B2
(45) Date of Patent: Mar. 2, 2010

(54) ACTIVATION AND EXPANSION OF T-CELLS USING AN AGENT THAT PROVIDES A PRIMARY ACTIVATION SIGNAL AND ANOTHER AGENT THAT PROVIDES A CO-STIMULATORY SIGNAL

(75) Inventors: James Riley, Downingtown, PA (US); Carl June, Merion Station, PA (US); Marcela Maus, Wynnewood, PA (US)

(73) Assignee: The Trustees of the University of Pennsylvania

( * ) Notice: Subject to any disclaimer, the term of this patent is extended or adjusted under 35 U.S.C. 154(b) by 642 days.

(21) Appl. No.: 10/336,135

(22) Filed: Jan. 3, 2003

(65) Prior Publication Data

US 2003/0147869 A1 Aug. 7, 2003

Related U.S. Application Data

(60) Provisional application No. 60/346,092, filed on Jan. 3, 2002.

(51) Int. Cl.
G01N 33/567 (2006.01)
G01N 33/53 (2006.01)
C12N 15/00 (2006.01)
C07K 16/00 (2006.01)

(52) U.S. Cl. ............ 435/7.1; 435/7.21; 435/7.24; 435/440

(58) Field of Classification Search ............... None
See application file for complete search history.

(56) References Cited

U.S. PATENT DOCUMENTS

| | | | |
|---|---|---|---|
| 5,166,320 A | 11/1992 | Wu et al. | |
| 5,190,878 A | 3/1993 | Wilhelm | |
| 5,529,921 A | 6/1996 | Peterson et al. | |
| 5,827,642 A | 10/1998 | Riddell et al. | |
| 5,858,358 A * | 1/1999 | June et al. | 424/130.1 |
| 5,888,807 A | 3/1999 | Palsson et al. | |
| 5,962,320 A | 10/1999 | Robinson | |
| 5,985,653 A | 11/1999 | Armstrong et al. | |
| 6,001,365 A | 12/1999 | Peterson et al. | |
| 6,096,532 A | 8/2000 | Armstrong et al. | |
| 6,352,694 B1 | 3/2002 | June et al. | |
| 6,355,479 B1 | 3/2002 | Webb et al. | |
| 6,464,973 B1 | 10/2002 | Levitsky et al. | |
| 6,534,055 B1 | 3/2003 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,890,753 B2 | 5/2005 | Flyer et al. | |
| 6,905,681 B1 | 6/2005 | June et al. | |
| 6,905,874 B2 | 6/2005 | Berenson et al. | |
| 7,175,843 B2 | 2/2007 | June et al. | |
| 2003/0224520 A1 | 12/2003 | June et al. | |
| 2004/0101519 A1 | 5/2004 | June et al. | |
| 2004/0110290 A1 | 6/2004 | June et al. | |
| 2004/0191235 A1 | 9/2004 | Groux et al. | |
| 2004/0241162 A1 | 12/2004 | Berenson et al. | |
| 2005/0003484 A1* | 1/2005 | Hirano et al. | 435/69.1 |
| 2006/0034810 A1 | 2/2006 | Riley et al. | |
| 2006/0121005 A1 | 6/2006 | Berenson et al. | |

FOREIGN PATENT DOCUMENTS

| | | |
|---|---|---|
| WO | WO 95/00642 | 1/1995 |
| WO | WO 95/03408 | 2/1995 |
| WO | WO95/33823 | 12/1995 |
| WO | WO 9936093 | * 7/1999 |
| WO | WO00/25813 | 5/2000 |
| WO | WO 02/092793 | 11/2002 |
| WO | WO 03/006632 | 1/2003 |
| WO | WO03/057171 | 7/2003 |
| WO | WO03/065977 | 8/2003 |

OTHER PUBLICATIONS

Green et. al. Antigen-specific human monoclonal antibodies from mice engineered with human Ig heavy and light chain YACs. Nat Genet. 1994; 7: 13-21.*

Thomas, A.K., et al.,"A cell-based artificial antigen-presenting cell coated with anti-CD3 and CD28 antibodies enables rapid expansion and long-term growth of CD4 T lymphocytes," *Clinical Immunology* 105(3): 259-272, (Dec. 2002).

Groux et al., "CD3-mediated apoptosis of human medullary thymocytes and activated peripheral T cells: respective roles of interleukin-1, interleukin-2, interferon-γ and accessory cells", *Eur. J. Immunol.* 23:1623-1629 (1993).

Kabelitz et al., "Life and death of a superantigen-reactive humand CD4[+] T cell clone: staphylococcal enterotoxins induce death by apoptosis but simultaneously trigger a proliferative response in the presence of HLA-DR[+] antigen-presenting cells", *International Immunology* 4:12, 1381-1388 (1992).

(Continued)

*Primary Examiner*—Maher M Haddad
*Assistant Examiner*—Chun Dahle
(74) *Attorney, Agent, or Firm*—Drinker Biddle & Reath LLP

(57) ABSTRACT

The present invention relates to compositions and methods for activating and expanding T-cells. The T-cells are induced to proliferate by providing a primary activation signal and a co-stimulatory signal to the T cells.

15 Claims, 13 Drawing Sheets

OTHER PUBLICATIONS

Zamai et al., "Lymphocyte binding to K562 cells: effect of target cell irradiation and correlation with ICAM-1 and LFA-3 expression", *Eur. J. Histochem.* 38:1, 53-60 (1994).

Almand, et al., "Clinical Significance of Defective Dendritic Cell Differentiation in Cancer", *Clinical Cancer Research* 6, pp. 1755-1766, May 2000.

Bamford, et al., "The 5' Untranslated Region, Signal Peptide, and the Coding Sequence of the Carboxyl Terminus of IL-15 Participate in Its Multifaceted Translational Control", *J. Immunol.* 160, pp. 4418-4426, 1998.

Bierer et al., "T Cell Receptors: Adhesion and Signaling", *Advance Cancer Research* 56, pp. 49-76, 1991.

Bretscher, "The two-signal model of lymphocyte activation twenty-one years later", *Immunol. Today* 13, pp. 74-76, 1992.

Brodie et al., "In vivo migration and function of transferred HIV-1-specific cytotoxic T cells", *Nat. Med.* 5:1, pp. 34-41, Jan. 1999.

Byun et al., "In Vitro Maturation of Neonatal Human CD8 T Lymphocytes into IL-- and IL-5-Producing Cells", *J. Immunol.* 153, pp. 4862-4871, 1994.

Chapoval et al., "B7-H3: A costimulatory molecule for T cell activation and IFN-γ production", *Nature Immunology* 2:3, pp. 269-274, Mar. 2001.

Claret et al., "Characterization of T Cell Repertoire in Patients with Graft-Versus-Leukemia After Donor Lymphocyte Infusion", *J. Clin. Invest.* 100:4, pp. 855-866, Aug. 1997.

Curtsinger et al., "$CD8^+$ Memory T Cells ($CD44^{high}$, $Ly$-$6C^+$) Are More Sensitive than Naïve Cells ($CD44^{low}$, $Ly$-$6C^-$) to TCR/CD8 Signaling in Response to Antigen", *J. Immunol.* 160, pp. 3236-3243, 1998.

Dahl et al., "Expression of Bcl-$X_L$ Restores Cell Survival, but Not Proliferation and Effector Differentiation, in CD28-deficient T Lymphocytes", *J. Exp. Med.* 191:12, pp. 2031-2037, Jun. 2000.

DeBenedette et al., "Costimulation of $CD28^-$ T Lymphocytes by 4-1BB Ligand", *J. Immunol.* 158, pp. 551-559, 1997.

Deeths et al., "B7-1-dependent co-stimulation results in qualitatively and quantitatively different responses by $CD4^+$ and $CD8^+$ T cells", *Eur. J. Immunol.* 27, pp. 598-608, 1997.

Deeths et al., "$CD8^+$ T Cells Become Nonresponsive (Anergic) Following Activation in the Presence of Costimulation", *J.Immunol.* 163, pp. 102-110, 1999.

Dong et al., "B7-H1, a third member of the B7 family, co-stimulates T-cell proliferation and interleukin-10 secretion", *Nature Medicine* 5:12, pp. 1365-1369, Dec. 1999.

Dudley et al., "Adoptive Transfer of Cloned Melanoma-Reactive T Lymphocytes for the Treatment of Patients with Metastatic Melanoma", *J. Immunother.* 24, pp. 363-373, 2001.

Dunbar et al., "Direct isolation, phenotyping and cloning of low-frequency antigen-specific cytotoxic T lymphocytes from peripheral blood", *Current Biology* 8, pp. 413-416, Mar. 1998.

Fraser et al., "Regulation of Interleukin-2 Gene Enhancer Activity by the T Cell Accessory Molecule CD28", *Science* 251, pp. 313-316, Jan. 1991.

Freeman et al., "Engagement of the PD-1 Immunoinhibitory Receptor by a Novel B7 Family Member Leads to Negative Regulation of Lymphocyte Activation", *J. Exp. Med.* 192:7, pp. 1027-1034, Oct. 2000.

Gett et al., "Cell division regulates the T cell cytokine repertoire, revealing a mechanism underlying immune class regulation", *Proc. Natl. Acad. Sci.U.S.A* 95, pp. 9488-9493, 1998.

Gett et al., "A cellular calculus for signal integration by T cells", *Nature Immunology* 1:3, pp. 239-244, Sep. 2000.

Gillis et al., "Long term culture of tumour-specific cytotoxic T cells", *Nature* 268, pp. 154-156, Jul. 1977.

Gimmi et al., "B-cell surface antigen B7 provides a costimulatory signal that induces T cells to proliferate and secrete interleukin 2", *Proc. Natl. Acad. Sci. USA* 88, pp. 6575-6579, Aug. 1991.

Goodwin et al., "Molecular cloning of a ligand for the inducible T cell gene 4-1BB: a member of an emerging family of cytokines with homology to tumor necrosis factor*", *Eur. J. Immunol.* 23, pp. 2631-2641, 1993.

Guinn et al., "4-1BB Cooperates with B7-1 and B7-2 in Converting a B Cell Lymphoma Cell Line into a Long-Lasting Antitumor Vaccine", *J. Immunol.* 162, pp. 5003-5010, 1999.

Hansen et al., "Monoclonal Antibodies Identifying a Novel T-Cell Antigen and Ia Antigens of Human Lymphocytes", *Immunogenetics* 10, pp. 247-260 1980.

Harding et al., "CD28-mediated signalling co-stimulates murine T cells and prevents induction of anergy in T-cell clones", *Nature* 356, pp. 607-609, Apr. 1992.

Heslop et al., "Long-term restoration of immunity against Epstein-Barr virus infection by adoptive transfer of gene-modified virus-specific T lymphocytes", *Nature Medicine* 2:5, pp. 551-555, May 1996.

Hurtado et al., "Potential Role of 4-1BB in T Cell Activation", *J. Immunol.* 155, pp. 3360-3367, 1995.

Hurtado et al., "Signals Through 4-1BB Are Costimulatory to Previously Activated Splenic T Cells and Inhibit Activation-Induced Cell Death", *J. Immunol.* 158, pp. 2600-2609, 1997.

Iezzi et al., "The Duration of Antigenic Stimulation Determines the Fact of Naïve and Effector T Cells", *Immunity* 8, pp. 89-95, Jan. 1998.

Jelley-Gibbs et al., "Two Distinct Stages in the Transition from Naïve CD4 T Cells to Effector, Early Antigen-Dependent and Late Cytokine-Driven Expansion and Differentiation", *J.Immunol.* 165, pp. 5017-5026, 2000.

Jenkins et al., "Molecules involved in T-cell costimulation", *Curr. Opin. Immunol.* 5, pp. 361-367, 1993.

June et al., "T-Cell Proliferation Involving the CD28 Pathway Is Associated with Cyclosporine-Resistant Interleukin 2 Gene Expression", *Molecular and Cellular Biology* 7, pp. 4472-4481, Dec. 1987.

June et al., "The B7 and CD28 receptor families", *Immunol.Today* 15, pp. 321-331, 1994.

Kawabe et al., "Programmed cell death and extrathymic reduction of $V\beta 8^+$ $CD4^+$ T cells in mice tolerant to *Staphylococcus aureus* enterotoxin B", *Nature* 349, pp. 245-248, Jan. 1991.

Ku et al., "Control of Homeostatis of $CD8^+$ Memory T Cells by Opposing Cytokines", *Science* 288, pp. 675-678, Apr. 2000.

Kung et al., "Monoclonal Antibodies Defining Distinctive Human T Cell Surface Antigens", *Science* 206, pp. 347-349, 1979.

Kurys et al., "The Long Signal Peptide Isoform and Its Alternative Processing Direct the Intracellular Trafficking of Interleukin-15*", *J. Biol. Chem.* 275:2, pp. 30653-30659, Sep. 2000.

Latchman et al., "PD-L2 is a second ligand for PD-1 and inhibits T cell activation", *Nature Immunology* 2:3, pp. 261-268, Mar. 2001.

Latouche et al., "Induction of human cytotoxic T lymphocytes by artificial antigen-presenting cells", *Nature Biotechnology* 18, pp. 405-409, Apr. 2000.

Laux et al., "Response Differences between Human $CD4^+$ and $CD8^+$ T-Cells during CD28 Costimulation: Implications for Immune Cell-Based Therapies and Studies Related to the Expansion of Double-Positive T-Cells during Aging", *Clinical Immunology* 96:3, pp. 187-197, Sep. 2000.

Lenschow et al., "Long-Term Survival of Xenogeneic Pancreatic Islet Grafts Induced by CTLA4Ig", *Science* 257, pp. 789-792, Aug. 1992.

Levine et al., "CD28 ligands CD80 (B7-1) and CD86 (B7-2) induce long-term autocrine growth of $CD4^+$ T cells and induce similar patterns of cytokine secretion in vitro", *International Immunology* 7:6, pp. 891-904, Jan. 1995.

Levine et al., "Antiviral Effect and Ex Vivo $CD4^+$ T Cell Proliferation in HIV-Positive Patients as a Result of CD28 Costimulation", *Science* 272, pp. 1939-1943, Jun. 1996.

Levine et al., "Effects of CD28 Costimulation on Long-Term Proliferation of $CD4^+$ T Cells in the Absence of Exogenous Feeder Cells", *J. Immunol.* 159, pp. 5921-5930, 1997.

Levine et al., "Adoptive transfer of costimulated $CD4^+$ T cells induces expansion of peripheral T cells and decreased CCR5 expression in HIV infection", *Nature Medicine* 8:1, pp. 47-53, Jan. 2002.

Li et al., "IL-15 and IL-2: a matter of life and death for T cells in vivo", *Nature Medicine* 7:1, pp. 114-118, Jan. 2001.

Lindsten et al., "Regulation of Lymphokine Messenger RNA Stability by a Surface-Mediated T Cell Activation Pathway", *Science* 244, pp. 339-343, Apr. 1989.

Linsley et al., "The Role of the CD28 Receptor During T Cell Responses to Antigen", *Annu. Rev. Immunol.* 11, pp. 191-212, 1993.

Lord et al., "The IL-2 Receptor Promotes Proliferation, bcl-2 and bcl-x Induction, But Not Cell Viability Through the Adaptor Molecule Shc", *J. Immunol.* 161, pp. 4627-4633, 1998.

Malefyt et al., "Direct Effects of IL-10 on Subsets of Human CD4+ T Cell Clones and Resting T Cells", *J. Immunol.* 150:11, pp. 4754-5765, Jun. 1993.

Marks-Konczalik et al., "IL-2-induced activation-induced cell death is inhibited in IL-15 transgenic mice", *Proc. Natl. Acad. Sci. U.S.A.* 97, pp. 11445-11450, 2000.

Maus et al., "Ex vivo expansion of polyclonal and anitgen-specific cytotoxic T lymphocytes by artificial APCs expressing ligands for the T-cell receptor, CD28 and 4-1BB", *Nature Biotechnology* 20, pp. 143-148, Feb. 2002.

Melero et al., "Monoclonal antibodies against the 4-1BB T-cell activation molecule eradicate established tumors", *Nature Medicine* 3:6, pp. 682-685, Jun. 1997.

Melero et al., "Amplification of tumor immunity by gene transfer of the co-stimulatory 4-1BB ligand: synergy with the CD28 co-stimulatory pathway", *Eur. J. Immunol.* 28, pp. 1116-1121, 1998.

Melief et al., "T-Cell Immunotherapy of Tumors by Adoptive Transfer of Cytotoxic T Lymphocytes and by Vaccination with Minimal Essential Epitopes", *Immunological Reviews* 146, pp. 167-177, 1995.

Musso et al., "Human Monocytes Consitutively Express Membrane-Bound, Biologically Active, and Interferon-γ-Upregulated Interleukin-15", *Blood* 93:10, pp. 3531-3539, 1999.

Pollok et al., "Inducible T Cell Angiten 4-1BB[1] : Analysis of Expression and Function", *J. Immunol.* 150:3, pp. 771-781, Feb. 1993.

Prakken et al., "Artificial antigen-presenting cells as a tool to exploit the immune 'synapse'", *Nature Medicine* 6:12, pp. 1406-1410, Dec. 2000.

Ribinovitch, "Regulation of human fibroblast growth rate by both noncycling cell fraction and transition probability is shown by growth in 5-bromodeoxyuridine followed by Hoechst 33258 flow cytometry", *Proc. Natl. Acad. Sci. USA* 80, pp. 2951-2955, May 1983.

Refaeli et al., "Biochemical Mechanisms of IL-2 Regulated Fas-Mediated T Cell Apoptosis", *Immunity* 8, pp. 615-623, May 1998.

Riddell et al., "The use of anti-CD3 and anti-CD28 monoclonal antibodies to clone and expand human antigen-specific T cells", *J. Immunological Methods* 128, pp. 189-201, 1990.

Riddell et al., "Restoration of Viral Immunity in Immunodeficient Humans by the Adoptive Transfer of T Cell Clones", *Science* 257, pp. 238-241, Jul. 1992.

Riddell et al., "Phase I study of cellular adoptive immunotherapy using genetically modified CD8+ HIV-specific T cells for HIV seropositive patients undergoing allogeneic bone marrow transplant", The Fred Hutchinson Cancer Research Center and the University of Washington School of Medicine, Department of Medicine, Division of Oncology, *Hum. Gene Ther.* 3, pp. 319-338, 1992.

Riddell et al., "Principles for Adoptive T Cell Therapy of Human Viral Diseases", *Annu. Rev. Immunol.* 13, pp. 545-586, 1995.

Riley et al., "ICOS Costimulation Requires IL-2 and Can Be Prevented by CTLA-4 Engagement", *J. Immunol.* 166, pp. 4943-4948, 2001.

Rooney et al., "Infusion of Cytotoxic T Cells for the Prevention and Treatment of Epstein-Barr Virus-Induced Lymphoma in Allogeneic Transplant Recipients", *Blood* 92:5, pp. 1549-1555, Sep. 1998.

Rosenberg et al., "Gene Transfer into Humans—Immunotherapy of Patients with Advance Melanoma, Using Tumor-Infiltrating Lymphocytes Modified by Retroviral Gene Transduction", *The New England Journal of Medicine*, pp. 570-578, Aug. 1990.

Sagerstrom et al., "Activation and differentiation requirements of primary T cells in vitro", *Proc. Natl. Acad. Sci. USA* 90, pp. 8987-8991, Oct. 1993.

Saoulli et al., "CD28-independent, TRAF2-dependent Costimulation of Resting T Cells by 4-IBB Ligand", *J. Exp. Med.* 187:11, pp. 1848-1862, Jun. 1998.

Schwartz, "A Cell Culture Model for T Lymphocyte Clonal Anergy", *Science* 248, pp. 13491356, 1990.

Schwartz, "Costimulation of T Lymphocytes: The Role of CD28, CTLA-4, and B7/BB1 in Interleukin-2 Production and Immunotherapy", *Cell* 71, pp. 1065-1068, Dec. 1992.

Shuford et al., "4-IBB Costimulatory Signals Preferentially Induce CD8+ T Cell Proliferation and Lead to the Amplification In Vivo of Cytotoxic T Cell Responses", *J. Exp. Med.* 186:1, pp. 47-55, Jul. 1997.

Smith et at, "T-Cell Growth Factor-Mediated T-Cell Proliferation", *Ann. N.Y. Acad. Sci.* 332, pp. 423-432, 1979.

Springer et al., "The Lymphocyte Function-Associated LFA-1, CD2, and LFA-3 Molecules: Cell Adhesion Receptors of the Immune System", *Ann. Rev. Immunol.* 5, pp. 223-252, 1987.

Tagaya et al., "Generation of secretable and nonsecretable interleukin 15 isoforms through alternate usage of signal peptides", *Proc. Natl. Acad. Sci. USA* 94, pp. 14444-14449, Dec. 1997.

Takahashi et at, "Cutting Edge: 4-1BB is a Bona Fide CD8 T Cell Survival Signal", *J. Immunol.* 162, pp. 5037-5040, 1999.

Tan et al., "4-1BB Costimulation Is Required for Protective Anti-Viral Immunity After Peptide Vaccination", *J. Immunol.* 164, pp. 2320-2325, 2000.

Tan, "Autoantibodies as reporters identifying aberrant cellular mechanisms in tumorigenesis", *J. Clin. Invest.* 108, pp. 1411-1415, Nov. 2001.

Tseng et al., "B7-DC, a New Dendritic Cell Molecule with Potent Costimulatory Properties for T Cells", *J. Exp. Med.* 193:7, pp. 839-845, Apr. 2001.

Turka et al., "T-cell activation by the CD28 ligand B7 is required for cardiac allograft rejection in vivo", *Proc. Natl. Acad. Sci. USA* 89, pp. 11102-11105, Nov. 1992.

van de Winkel et al., "Human IgG Fc receptor heterogeneity: molecular aspects and clinical implications", *Immunol. Today* 14, pp. 215-221, 1993.

Van Parijs et al., "Uncoupling IL-2 Signals that Regulate T Cell Proliferation, Survival, and Fas-Mediated Activation-Induced Cell Death", *Immunity* 11, pp. 281-288, Sep. 1999.

Voltz et al., "A Serologic Marker of Paraneoplastic Limbic and Brain-Stem Encephalitis in Patients with Testicular Cancer", *N. Engl. J. Med.* 340, pp. 1788-1795, Jun. 1999.

Wang et al., "Naïve CD8+ T Cells Do Not Require Costimulation for Proliferation and Differentiation into Cytotoxic Effector Cells", *J. Immunol.* 164, pp. 1216-1222, 2000.

Webb et al., "Extrathymic Tolerance of Mature T Cells: Clonal Elimination as a Consequence of Immunity", *Cell* 63, pp. 1249-1256, Dec. 1990.

Wells et al., "Following the Fate of Individual T Cells throughout Activation and Clonal Expansion: Signals from T Cell Receptor and CD28 Differentially Regulate the Induction and Duration of a Proliferative Response", *J. Clin. Invest.* 100:12, pp. 2173, 3183, Dec. 1997.

Wells et al., "T Cell Effector Function and Anergy Avoidance Are Quantitatively Linked to Cell Division", *J. Immunol.* 165, pp. 2432-2443, 2000.

Yee et al., "Isolation of High Avidity Melanoma-Reactive CTL from Heterogeneous Populations Using Peptide-MHC Tetramers", *J. Immunol.* 162, pp. 2227-2234, 1999.

Yee et al., "Melanocyte Destruction after Antigen-specific Immunotherapy of Melanoma: Direct Evidence of T Cell-mediated Vitiligo", *J. Exp. Med.* 192:11, pp. 1637-1643, Dec. 2000.

Yee et al., "In vivo tracking of tumor-specific T cells", *Curr. Opin. Immunol.* 13, pp. 141-146, 2001.

Abendroth et al., 2000, J Gen Viral 81(Pt 10):2375-2383.
Afanasyeva et al., 2001 Circulation 104(25):3145-3151.
Alexander-Miller, et al., 1996, Proc Natl Acad Sci USA 93(9):4102-4107.
Altman et al., 1996, Science 274(5284):94-96.
ATCC Cell Lines and Hybridomas 1994 8th Edition, p. 129.
Assoian et al., 1987, Proc Natl Acad Sci USA 84(17):6020-6024.
Bretscher, 1992, Immunol Today 13:74-76.
Britten et al., 2002, J Immunol Methods 259(1-2):95-110.
Carroll et al., 1997, Science 276 (5310):273-276.
Coyle et al., 2000, Immunity 13(1):95-105.
Curiel, 2004, Nat Med 10(9):942-949.
Deeks et al., 2002, Mol Ther 5(6):788-797.

Dietz et al., 2001, Cytotherapy 3(2):97-105.
Dull et al., 1998, J Virol 72(11):8463-8471.
Esslinger et al., 2002, Hum Gene Ther 13(9):1091-1100.
Fanger et al., 1996, J Immunol 157(2):541-548.
Flamand et al., 1998, Proc Natl Acad Sci USA 95(6):3111-3116.
Gonzalo et al., 2001, Nat Immunol, 2(7):597-604.
Grosenbach et al., 2003, Cell Immunol 222(1):45-57.
Gupta et al., 1999, J Leukoc Biol 66(1):135-143.
Hoffmann et al., 2004, Blood 104(3):895-903.
Hutloff et al., 1999, Nature 397(6716):263-266.
Imlach et al., 2001 J Virol 75(23):11555-11564.
Kahl et al., 2004, J Virol 78(3):1421-1430.
Kato et al., 1998, J Clin Invest 101(5):1133-1141.
Koenig et al., 1995, Nat Med 1(4):330-336.
Krummel 1996, J Exp Med 183(6):2533-2540.
Lee et al., 2002, Vaccine 20:A8-A22.
Lieberman et al., 1997, Blood 90(6):2196-2206.
Liebowitz et al., 1998 Curr Opin Oncol 10(6):533-541.
Lozzio, 1975, Blood, 45(3):321-334.
Maus et al., 2003 Clin Immunol 106(1):16-22.
Mitsuyasu et al, 2000, Blood 96(3):785-793.
Muller et al., 1999, Immunology 97(2):280-286.
Niethammer et al., 2002, Vaccine 20(3-4):421-429.
O'Doherty et al., 2000 J Virol 74(21):10074-10080.
Oh et al., 2003 J Immunol 170(5):2523-2530.
Parry et al., 2003, J Immunol 171(1):166-174.
Qiao et al., 1999 Cancer Gene Ther 6(4):373-379.
Ranga et al., 1998, Proc Natl Acad Sci USA 95(3):1201-1206.
Ranheim et al., 1993, J ,Exp Med 177(4):925-935.
Riddell et al., 1996, Nature Med 2(2):216-223.
Riddell et al., 2000, Cancer J 6:S250-S258.
Riley et al., 1997, J. Immunol 158(11):5545-5553.
Rooney et al., 1995, Lancet 345(8941):9-13.
Rosenberg et al. 1988, N Engl J Med 319(25):1676-1680.
Sakaguchi, 2005, Nat Immunol 6(4):345-352.
Salomon, 2000, Immunity 12(4):431-440.
San Jose et al., 1998, Eur J Immunol 28(1):12-21.
Schlienger et al., 2000, Blood 96(10):3490-3498.
Scholler et al., 2001, J Immunol 166(6):3865-3872.
Scholler et al., 2002, J Immunol 168(6):2599-2602.
Schwartz et al., 2001, Nature, 410(6828):604-608.
Schwartz et al., 2002, Nat Immunol 3(5):427-434.
Shedlock et al., 2003, Science 300:337-339.
Shibuya et al., 1999, Arch Otolaryngol Head Neck Surg. 125(11):1229-1234.
Stripecke et al., 2000, Blood 96(4):1317-1326.
Sun et al., 2003, Science 300:339-342.
Topp et al., 2003, J Exp Med 198(6):947-955.
Viguier et al., 2004, J Immunol 173(2):1444-1453.
Vieweg et al., 2004 Expert Opin Biol Ther 4(11):1791-1801.
Vonderheide et al., 1999, Immunity, 10(6):673-679.
Vonderheide et al., 2003, Immunol Res 27(2-3):341-356.
Vonderheide et al., 2004, Clin Cancer Res. 10(3):828-839.
Walker et al., 2000, Blood 96(2):467-474.
Walter et al., 1995, N Engl J Med 333(16):1038-1044.
Wakasugi et al., 1983 Proc Natl Acad Sci USA 80(19):6028-6031.
Warrington et al., 2003, Blood 101(9):3543-3549.
Weng et al., 1997, J Immunol 158(7):3215-3220.
Yee et al., 2002, Proc Natl Acad Sci USA 99(25):16168-16173.
Yotnda et al. 1998, J Clin Invest 101(10)2290-2296.
Zajac et al., 1998, J Exp Med 188:2205-2213.
Zhang et al., 2004, Immunity 20(3):337-347.
Zhu et al., 2001 J Immunol, 167(5):2671-2676.
Zufferey et al., 1998, J Virol 72(12):9873-9880.

* cited by examiner

ACTIVATION AND EXPANSION OF T-CELLS USING AN AGENT THAT PROVIDES A PRIMARY ACTIVATION SIGNAL AND ANOTHER AGENT THAT PROVIDES A CO-STIMULATORY SIGNAL

REFERENCE TO RELATED APPLICATIONS

This application claims priority to U.S. Provisional Application 60/346,092, filed Jan. 3, 2002, the contents of which are herein incorporated by reference. Related to the present application are simultaneously filed U.S. patent application Ser. No. 10/336,224 and International Application No. PCT/US03/00339, each of which is herein incorporated by reference.

FIELD OF THE INVENTION

The invention relates to the priming and expansion of cytotoxic T lymphocytes (CTLs), particularly human CTLs, in response to artificial antigen presenting cells, and use of the activated CTLs as an immunotherapeutic treatment for cancer and infectious diseases.

BACKGROUND OF THE INVENTION

Immunotherapy involving the priming and expansion of cytotoxic T lymphocytes (CTLs) holds promise for the treatment of cancer and infectious diseases, particularly in humans (Melief et al.,*Immunol. Rev.* 145:167-177 (1995); Riddell et al., *Annu. Rev. Immunol.* 13:545586 (1995). Current studies of adoptive transfer in patients with HIV, CMV, and melanoma involve the infusion of T cells that have been stimulated, cloned and expanded for many weeks in vitro on autologous dendritic cells (DC), virally infected B cells, and/or allogeneic feeder cells (Riddell et al., *Science* 257:238-241 (1992); Yee et al., *J. Exp. Med.* 192:1637-1644 (2000); Brodie et al.,*Nat. Med.* 5:34-41 (1999); Riddell et al., *Hum. Gene Ther.* 3:319-338 (1992), Riddell et al., *J. Immunol. Methods* 128:189-201 (1990)). However, adoptive T cell immunotherapy clinical trials commonly use billions of cells (Riddell et al., 1995). In order to produce these quantities of cells, 1000-4000 fold expansion of T cells in vitro (10-12 population doublings) is usually required. Furthermore, for optimal engraftment potential and possible therapeutic benefit, it is important to ensure that the T cells, after in vitro expansion, are functional, and not senescent, at the time of re-infusion.

T cell activation is initiated by the engagement of the T cell receptor/CD3 complex (TCR/CD3) by a peptide-antigen bound to a major histocompatibility complex (MHC) molecule on the surface of an antigen-presenting cell (APC) (Schwartz, *Science* 248:1349 (1990)). While this is the primary signal in T cell activation, other receptor-ligand interactions between APCs and T cells are required for complete activation. For example, TCR stimulation in the absence of other molecular interactions can result in an inability of the T cells to respond to full activation signals upon re-stimulation (Schwartz, 1990; Harding, et al., *Nature* 356:607 (1992)). In the alternative, T cells die by programmed cell death (apoptosis) when activated by TCR engagement alone (Webb et al., *Cell* 63:1249 (1990); Kawabe et al., *Nature* 349:245 (1991); Kabelitz et al., *Int. Immunol.* 4:1381 (1992); Groux et al., *Eur. J. Immunol.* 23:1623 (1993)).

Multiple receptor-ligand interactions take place between the T cell and the APC, many of which are adhesive in nature, reinforcing the contact between the two cells (Springer et al., *Ann. Rev. Immunol.* 5:223 (1987)), while other interactions transduce additional activation signals to the T cell (Bierer e al., *Adv. Cancer Res.* 56:49 (1991)). CD28, a surface glycoprotein present on 80% of peripheral T cells in humans, is present on both resting and activated T cells. CD28 binds to B7-1 (CD80) or B7-2 (CD86) and is the most potent of the known co-stimulatory molecules (June et al.,*Immunol. Today* 15:321 (1994); Linsley et al., *Ann. Rev. Immunol.* 11:191 (1993)). Moreover, CD28 ligation on T cells in conjunction with TCR engagement induces the production of IL-2 molecules (June et al., 1994; Jenkins et al., 1993; Schwartz, 1992), which are critical for continued proliferation.

Co-stimulation of T cells has been shown to affect multiple aspects of T cell activation (June et al., 1994). It lowers the concentration of anti-CD3 required to induce a proliferative response in culture (Gimmi et al., *Proc. Natl. Acad. Sci. USA* 88:6575 (1991)). CD28 costimulation also markedly enhances the production of lymphokines by helper T cells through transcriptional and post-transcriptional regulation of gene expression (Lindsten et al., *Science* 244:339 (1989); Fraser et al., *Science* 251:313 (1991)), and can activate the cytolytic potential of cytotoxic T cells. Inhibition of CD28 co-stimulation in vivo can block xenograft rejection, and allograft rejection is significantly delayed (Lenschow et al., *Science* 257:789 (1992); Turka et al., *Proc. Natl. Acad. Sci. USA* 89:11102 (1992)).

However, methods of cloning and expanding T cells for adoptive immunotherapy have proven to have certain drawbacks. The standard culture of pure $CD8^+$ cells is limited by apoptosis, and obtaining a sufficient number of cells to be useful has been particularly difficult. Current cell culture techniques require several months to produce sufficient numbers of cells from a single clone (Riddell et al., 1992; Heslop et al., *Nat. Med.* 2:551-555 (1996)), which is a problematic limiting factor in the setting of malignancy. Indeed, it is possible that the T cells that are currently infused into patients, may have a limited replicative capacity, and therefore, could not stably engraft to provide long-term protection from disease.

While previous investigators have noted long term qualitative persistence of CTLs in human adoptive transfer protocols, the quantitative level of sustained engraftment has been low (Rosenberg et al., *N. Engl. J. Med.* 323:570-578 (1990); Dudley et al., *J. Immunother.* 24:363-373 (2001); Yee et al., *Curr. Opin. Immunol.* 13:141-146 (2001); Rooney et al., *Blood* 92:1549-1555 (1998)). Therefore, the present invention offers therapeutic implications because there remains an unmet need for sustained high-level engraftment of human CTLs.

The inventors have previously shown that magnetic beads coated with anti-CD3 and anti-CD28 antibodies can be used as artificial antigen presenting cells (APCs) to support the long-term growth of $CD4^+$ T cells (U.S. Pat. No., 6,352,694; Levine et al., *J. Immunol.* 159:5921-5930 (1997); Latouche, et al., *Nat. Biotechnol.* 18:405-409 (2000)). However, it was subsequently shown by the inventors and others that beads or plates coated with anti-CD3 and anti-CD28 antibodies cannot support long-term growth of purified $CD8^+$ T cells (Deeths et al., *J. Immunol.* 163:102-110 (1999); Laux et al., *Clin. Immunol.* 96:187-197 (2000)). The $CD8^+$ T cells stimulated with anti-CD3/CD28 initially produce IL-2, but unlike $CD4^+$ T cells, become unresponsive when re-stimulated in vitro with anti-CD3 and anti-CD28. Moreover, this limitation cannot be overcome by the addition of IL-2 to the culture medium (Deeths et al., *Eur. J. Immunol.* 27:598-608 (1997)), and Bcl-xL induction alone, without complete IL-2 receptor signaling, is not sufficient to mediate cell survival or growth (Lord et al., *J. Immunol.* 161:4627-4633 (1998); Dahl et al., *J.*

*Exp. Med.* 191, 2031-2038 (2000)). Additional limitations of using the bead-based system on a wide-scale basis include: the high cost of the beads, the labor intensive process involved in removing the beads from the culture before infusion, and the inability of the beads to expand T cells (Deeths et al., 1999; Laux et al., 2000), plus the bead based system is restricted by a need for GM quality control approval before the start of each application The TNF receptor family member 4-1BB (CD137) was initially identified by receptor screens of activated lymphocytes (Pollok et al., *J. Immunol.* 150:771-781 (1993)). The 4-1BB ligand is expressed by activated B cells, dendritic cells, and monocytes/macrophages, all of which can act as APCs (Goodwin et al., *Eur. J. Immunol.* 23:2631-2641 (1993)). Previous studies have shown that stimulation of 4-1BB on $CD8^+$ T cells prolongs survival of CTLs in vivo and amplifies $CD8^+$-dependent immune responses in mice (Shuford et al., *J. Exp. Med.* 186:47-55 (1997)). Moreover, as a co-stimulatory molecule in the activation of T cells, 4-1BB signaling is independent from, albeit weaker than, CD28 signaling (Deeths et al., 1997; Hurtado et al., *J. Immunol.* 158:2600-2609 (1997); Hurtado et al., *J. Immunol.* 155, 3360-3367 (1995); Saoulli et al. *J. Exp. Med.* 187:1849-1862 (1998)). Consistent with these data, co-stimulation of 4-1BB has been shown to have anti-viral and anti-tumor effects (Tan et al., *J. Immunol.* 164:2320-2325 (2000); Melero et al., *Nat. Med.* 3:682-685 (1997); Melero et al., *Eur. J. Immunol.* 28, 1116-1121 (1998); DeBenedette et al., *J. Immunol.* 158:551-559 (1997); Guinn et al., *J. Immunol.* 162:5003-5010 (1999)).

Progress in designing more efficient T cell expansion systems will be a direct result of an improved understanding of T cell activation. Thus, there has been a long-felt need to find a cell based system that can promote long-term growth of activated CTL cells in a more amenable and effective manner than by means of the bead-based system. A cell based artificial APC would be more amenable to test the influence of cytokines and other co-stimulatory molecules than has been previously possible using microspheric artificial APCs. Such a system would also permit testing of the ability of natural ligands, rather than antibodies, to stimulate T cells.

SUMMARY OF THE INVENTION

This invention comprises system and methods for selectively inducing expansion of a population of T cells in the absence of exogenous growth factors, such as lymphokines, and accessory cells for use in research. The cell based expansion system and methods permit the long-term growth of CTLs, preferably human CTLs. In addition, T cell proliferation can be induced without the need for antigen, thus providing an expanded T cell population that is polyclonal with respect to antigen reactivity. In accordance with the invention, a population of T cells is induced to proliferate ex vivo or in vivo by activating the T cells and stimulating an accessory molecule on the surface of the T cells with a ligand that binds the accessory molecule. The system and methods provide for sustained proliferation of a selected population of, e.g., $CD4^+$ or $CD8^+$ or other T cell populations, over an extended period of time to yield a multi-fold increase in the number of these cells relative to the original T cell population, thus overcoming the difficulty in obtaining sufficient numbers of CTLs. See also, Maus et al., *Nat. Biotechnol.* 20:143-148 (2002); Thomas et al., in press 2003.

It is an object of the invention to provide artificial antigen presenting cells (APC) engineered by the inventors to mimic dendritic cells in their ability to stimulate rapid CTL growth, thus creating a universal artificial cell-based (APC) system that overcomes limitations of the prior art bead-based system for research purposes. Briefly, in accordance with this invention, cells are used rather than beads to promote long term growth of T cells in vivo. The K562 erythromyeloid cell line was used as a scaffold, engineered to stably express the human low-affinity Fcγ receptor, CD32, and the co-stimulatory molecule human (h) 4-1BB ligand (4-1BBL). Soluble anti-CD3 and anti-CD28 antibodies (Ab) were used to coat the K562 surface via binding CD32 before the T cells were added. Thus, K562-CD32-4-1BBL cells coated with anti-CD3 and anti-CD28 antibodies are used as artificial APCs to stimulate the long-term growth of functional polyclonal and antigen-specific human CTLs. In $CD8^+$ T cells the ability to expand long term was dependent upon having 4-1BBL on the K562 surface.

The addition of 4-1BBL as a co-stimulatory surface molecule was shown to express ligands for the T cell receptor and maintain diversity in T cell cultures. The resulting artificial APCs reproducibly activate and rapidly expand polyclonal or antigen-specific $CD8^+$ T cells, although the starting repertoire of $CD8^+$ T cells was preserved during culture. Furthermore, by using this approach to eliminate the problem of apoptosis of cultured $CD8^+$ T cells, significant therapeutic opportunities are created for adoptive immunotherapy.

T cells in which the level of marker proteins, such as Bcl-xL or IL-2, is modulated, i.e., preferably enhanced to augment cell proliferation, according to the system and methods of the invention, can be endogenous T cells present in a subject. The system and methods of the invention are thus useful for modulating immune responses, i.e., boosting or repressing immune responses. Accordingly, the methods of the invention have numerous applications, such as stimulating an immune reaction (for example to fight an infection) or stimulating survival of T cells whose life span is reduced (for example as a result of an infection, such as an infection with a human immunodeficiency virus).

It is a further object to provide methods for producing the aAPC for use for research purposes and a system for use thereof.

It is also an object to provide a system for inducing a population of T cells to rapidly proliferate long term to sufficient numbers for use in research. Also provided is a method for inducing a population of T cells to rapidly proliferate exponentially for a long term to sufficient numbers for research purposes, comprising activating the population of T cells by contacting the T cells ex vivo with at least one exogenous first agent that provides a primary activation signal to the T cells; and stimulating the activated T cells with at least one second agent that provides a co-stimulatory signal, such that T cells that have received a primary activation signal are stimulated to rapidly proliferate.

It is yet another object to provide a method for stimulating a population of $CD8^+$ T cells to rapidly proliferate exponentially for a long term, comprising primarily activating the population of $CD8^+$ T cells by contacting the $CD8^+$ T cells ex vivo with at least one exogenous first agent which stimulates a T cell receptor/CD3 complex-associated signal in the T cells; and stimulating the activated T cells with at least one second agent which is a ligand providing a co-stimulatory signal, such that T cells that have received the primary activation signal are stimulated to rapidly proliferate.

In addition, it is an object to provide a method of inducing a population of T cells from a subject to rapidly proliferate exponentially for a long term to sufficient numbers for research purposes, comprising isolating a population of T cells from a subject, activating the population of T cells by contacting the T cells ex vivo with at least one exogenous first agent that provides a primary activation signal to the T cells; and stimulating the activated T cells with at least one second agent that provides a co-stimulatory signal, such that T cells that have received a primary activation signal are stimulated to rapidly proliferate. In particular, it is an object to provide such a method when the subject is human, and wherein the method further comprises using the activated T cells to identify antigens in the subject. Moreover, when the subject is infected with a disease or condition, having at least one antigen related thereto, the provided method further comprises using the activated T cells to identify the at least one antigen. The antigen may comprise, e.g., and without limitation, a tumor antigen, an antigen relating to an autoimmune disorder or condition, or an infectious disease or pathogen. The method further comprises screening the at least one antigen as a target molecule for research purposes, or for developing a vaccine based upon the at least one antigen.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) that are presently preferred. It should be understood, however, that the invention is not limited to the precise arrangements and instrumentalities shown.

FIG. 1A depicts two-color flow-cytometric analysis of MHC I and II expression and CD54 and CD58 expression in parental K562 cells (top panels). Expression of CD32 and 4-1BBL in K32 (left) and K32/4-1BBL (right) cell lines is shown (middle panels). Isotype controls for the anti-CD32 antibody (IgG2a) and anti-4-1BBL antibody (IgG1) are shown for each aAPC (bottom panels). FIG. 1B depicts the engineered K32/4-1BBL aAPC interacting with a $CD8^+$ T cell. FIG. 1C graphically depicts proliferation of polyclonal $CD4^+$ and $CD8^+$ T cells stimulated with the indicated aAPCs, measured by [3H]thymidine incorporation between days 3 and 4 culture. T cells were stimulated with aAPCs as indicated, in the absence of cytokines. At 72 hours the cells were pulsed with [3H]thymidine and incubated for an additional 18 hours before harvesting. Counts per minute values are shown as mean±s.e.m. from triplicate cultures.

FIG. 2A graphically depicts $CD8^+$ T cells stimulated with CD3/28 beads (X), irradiated K32 cells loaded with CD3/28 antibodies (Δ), or with irradiated K32/4-1BBL cells loaded with CD3/28 antibodies (●). T cells were stimulated with aAPCs on days 0, 10, and 20 of culture. FIGS. 2B, 2C depict the purity of T cells and the fate of irradiated K32/4-1BBL stimulator cells assessed by staining for CD3, CD8 (FIG. 2B), and CD32 (FIG. 2C) expression during the first 7 days of culture. Variable numbers of red blood cells and platelets were contained in the input cultures; gating on cell size/debris was not used in this experiment so that all cells in the culture were represented. Viable cells are indicated by gating on propidium iodide to exclude dead cells. Results are representative of >10 different experiments, each with a different donor.

FIG. 3A is a schematic of the experimental protocol of the present invention. FIG. 3B depicts the specificity of cell cultures as assessed by MHC tetramer staining. $CD8^+$ T cells were stained with anti-CD8 antibody (x-axis) and A*0201 tetrameric MHC (y-axis) loaded with influenza matrix protein peptide (fluMP). Left panel of 3B: initial cell population of T cells on day 0, with gates showing the cells into $CD8^+$ flu-tet$^+$ and $CD8^+$flu-tet$^-$ populations. Right panels of 3A: tetramer staining of $CD8^+$flu-tet$^+$ (top) or $CD8^+$flu-tet$^-$ (bottom) cultures after expansion on K32/4-1BBL cells for 26 days. FIG. 3C graphically depicts a growth curve of the sorted $CD8^+$ T-cell populations. T cells were sorted into $CD8^+$ fluMP tetramer$^+$ (•) or $CD8^+$ fluMP tetramer$^-$ (□). The sorted T-cell populations were then stimulated with irradiated K32/4-1BBL cells loaded with CD3/28 antibodies as indicated (arrows). rIL-2 was added to the cultures beginning on day 28. The total cell numbers are depicted in a semi-log plot of cell number v. days in culture.

DESCRIPTION OF PREFERRED EMBODIMENTS OF THE INVENTION

Figure 1A:
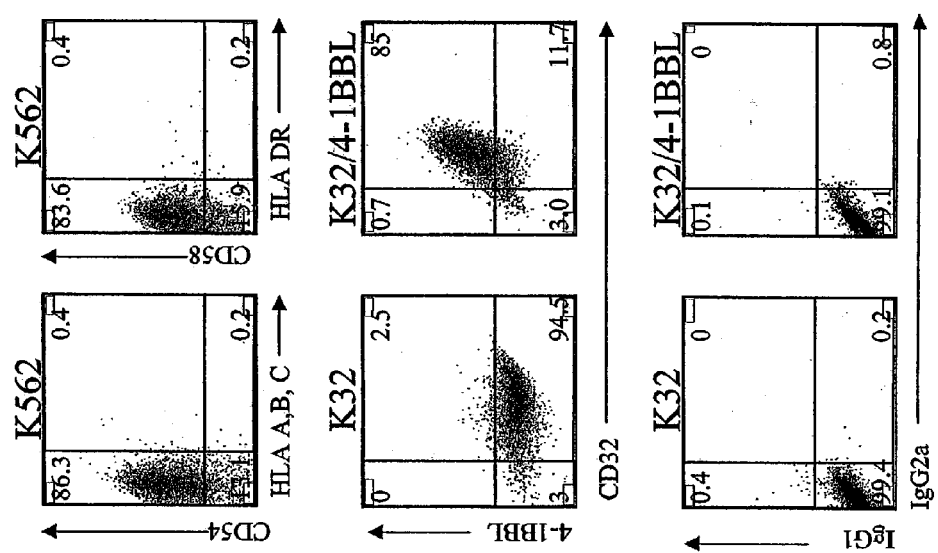
FIGS. 1A-1C depict construction of artificial APCs (aAPC) from the parental K562 cell line.
Figure 1B:
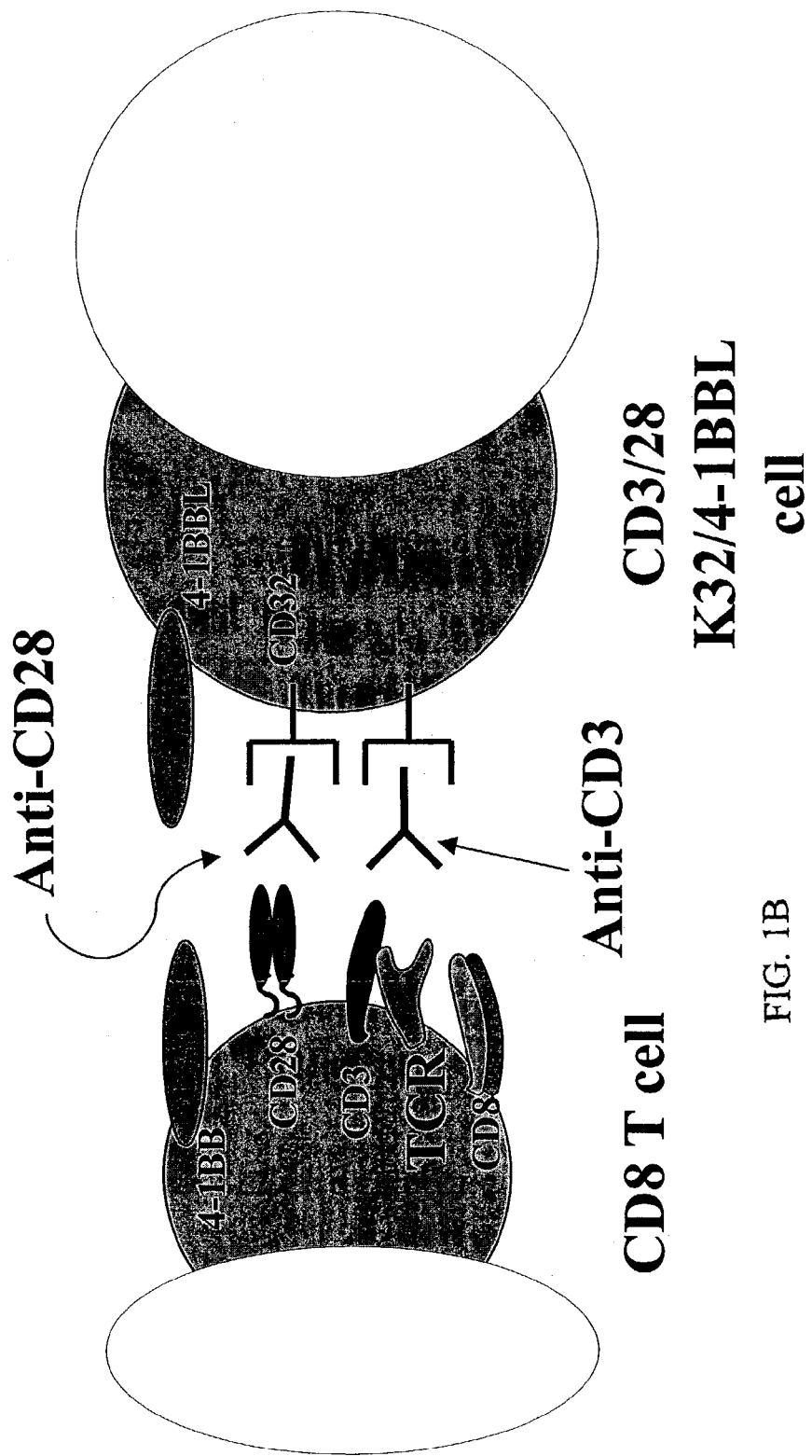

The system and methods of the present invention enable the selective stimulation of a T cell population to rapidly proliferate and expand exponentially to significant numbers in vivo in the absence of exogenous growth factors or accessory cells for use in research. Interaction between the T cell receptor (TCR)/CD3 complex and antigen presented in conjunction with either major histocompatibility complex (MHC) class I or class II molecules on an antigen-presenting cell (APC) initiates a series of biochemical events termed "antigen-specific T cell activation." The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event that initiates an immune response by the T cell.

In accordance with the present invention, a cell-based system is provided, whereby sufficient numbers of CTLs are produced using artificial antigen presenting cells (APCs) engineered by the inventors ex vivo to mimic dendritic cells in their ability to stimulate rapid CTL growth. Thus, a universal artificial cell-based (APC) system has been created that overcomes limitations of the prior art bead-based system for stimulating T cells.

Although stimulation of the TCR/CD3 complex or CD2 molecule is required for delivery of a primary activation signal in a T cell, a number of molecules on the surface of T cells, interchangeably termed "co-stimulatory molecules" or "co-stimulators," have been implicated in regulating the transition of a resting T cell to blast transformation, and subsequent proliferation and differentiation. Thus, in addition to the primary activation signal provided through the TCR/CD3 complex, induction of T cell responses requires a second co-stimulatory signal. For all polyclonal T cells, the anti CD3 antibody is sufficient to initiate activation. However, the proliferation is not be sustained and the cells typically die within about 6 days. When CD28 is added, the T cells survive for considerably longer, but will still die without the addition of a secondary co-stimulatory agent. As a stimulator, CD28 is believed to initiate or regulate a signal transduction pathway that is distinct from those stimulated by the TCR complex.

A particularly preferred second co-stimulator for the proliferation of $CD8^+$ T cells is the ligand 4-1BB, which has been shown to permit the cells to continue to proliferate for at least 6-8 months without signs of significant apoptosis (data not shown). The selected $CD8^+$ T cells treated with the artificial APC of the present invention (K32-CD3-CD28-4-1BBL) appear to proliferate in vitro for considerably longer than 8 months or a year, and starting with a population of $1\times10^4$ cells have already expanded beyond 12 logs in viable number. Moreover the cell expansion by the present invention has proven to be rapid (one donor's cells completed 31.5 population doublings in 67 days, equal to a 3 billion fold expansion, and the cells remain functional (via $^{51}Cr$ release) and viable, continuing to divide exponentially).

In one embodiment of the invention, the first co-stimulator is delivered ex vivo into a specific cell in the form of a soluble molecular APC complex. The complex contains the co-stimulator, alone or releasably bound to a carrier comprising a cell-specific binding agent which binds to a surface molecule of the specific cell and is of a size that can be subsequently internalized by the cell. Such complexes are described, e.g., in U.S. Pat. No. 5,166,320.

In another embodiment, the system and method of the invention involve enhancing the proliferation of a selected T cell population by contacting the T cells with at least one co-stimulatory agent that increases protein level of a recognized marker, such as IL-2 or Bcl-xL, in the T cell. The language "stimulate expression of the endogenous gene" is intended to include affecting the marker gene in the T cell, such that the level of the marker protein encoded by the gene is increased in the cell in direct correlation with the enhanced long term proliferation of the cells. The language "stimulate the transcription" is intended to include effecting transcription, such that the amount of transcribed marker mRNA is also increased. The term "endogenous marker gene" is intended to mean the marker gene, preferably IL-2 or Bcl-xL, which is naturally in the T cell, as opposed to an "exogenous marker gene" which as been introduced into the T cell.

In a preferred embodiment of the invention, a T cell is contacted with at least one co-stimulatory agent that results in the in vivo augmentation of marker protein levels in the T cells, enhancing proliferation of the T cells, and protection of the T cells against cell death. In a preferred embodiment, long term proliferation of a selected population of T cells is enhanced by contacting the T cells with a combination of agents that stimulate T cell proliferation with minimal or no apoptosis. "Minimal apoptosis" in this invention means that, as compared with proliferating T cells using a prior art system, apoptosis is significantly reduced, to the point that there is none at all, or if any residual apoptosis remains, the level is not sufficient to diminish augmentation of T cell proliferation produced by the present invention.

A preferred combination of agents is a combination of at least two agents that comprise co-stimulatory agents that activate the T cell. For example, activated T cell long term proliferation can be enhanced by contacting the T cell with a first agent that provides a primary activating signal to the T cell, and a second agent that provides a co-stimulatory signal to the T cell. A much preferred combination comprises at least a first agent that activates the T cell receptor and at least a second agent, such as a ligand, that provides a co-stimulatory signal to the T cell, so that T cell proliferation and marker protein levels are rapidly increased in the T cell. For $CD8^+$ cells, the most preferred ligand is 4-1BBL.

The language "primary activation signal" is intended to include signals, typically triggered through the T cell receptor (TCR)/CD3 and/or CD28 complex, that induce activation of T cells. Activation of a T cell is intended to include modifications of a T cell, such that the T cell is induced to proliferate and differentiate upon receiving a second signal, such as a co-stimulatory signal. In a specific embodiment, the primary activation signal is provided by an agent that contacts the T cell receptor, or the CD3 and/or CD28 complex associated with the T cell receptor. In a preferred embodiment, the primary activating signal is provided by an artificial APC. Thus, it is possible to selectively stimulate growth of an antigen-specific T cell clones in a population of T cells by contacting the T cells with one or more antigens on one or more APCs, and a second agent, which provides a co-stimulatory signal.

In a preferred embodiment of the invention, the T cells are stimulated with a combination of agents that stimulate both a primary activation signal and a co-stimulatory signal in the T cell. The term "co-stimulatory agent" is intended to include one or more agents that ex vivo provide a co-stimulatory signal in T cells, such that a T cell that has received a primary activation signal (e.g. an activated T cell) is stimulated to proliferate or to secrete cytokines, such as, but not limited to, IL-2, IL-4, IL-12, IL-15, IL-21 or interferon-gamma. Consequently, use of IRES vectors will allow linkage of cytokine secretion with T cell surface expression, thereby allowing the introduction of IL-2, IL-4, IL-12, IL-15, IL-21 and the like among others T cell expansion systems.

In a specific embodiment, the co-stimulatory agent interacts with CD3 and/or CD28 molecules on the surface of the T cells. In an even more preferred embodiment, the co-stimulatory signal is a ligand of CD3 and/or CD28. The language "stimulatory form of a natural ligand" of CD3 and/or CD28 is intended to include 4-1BBL molecules, fragments thereof, or modifications thereof, which are capable of providing co-stimulatory signals to the activated T cells. Stimulatory forms of natural ligands of CD3 and/or CD28 can be identified by, for example, contacting activated T cells with a form of a natural ligand of CD3 and/or CD28 and performing a standard T cell proliferation assay. Thus, a stimulatory form of a natural ligand of CD3 and/or CD28 is capable of ex vivo stimulation resulting in rapid and long term proliferation of the T cells. Stimulatory forms of natural ligands as utilized herein are described, for example, in PCT Publication No. WO 95/03408.

Other agents that can be used in conjunction with the present invention to enhance T cell growth include agents that stimulate one or more intracellular signal transduction pathways involved in T cell activation and/or co-stimulation, such as a calcium ionophore, an agent which stimulates protein kinase C, such as a phorbol ester, or a combination of a calcium ionophore and a phorbol ester. The stimulatory agent can also be one that activates protein tyrosine kinases. Other agents that can be employed to stimulate T cell proliferation in conjunction with the present invention, include agents such as polyclonal activator or activators, including agents that bind to glycoproteins expressed on the plasma membrane of T cells; lectins, such as phytohemaglutinin, concanavalin (Con A) and pokeweed mitogen, or lymphokines, alone or in combination with another agent.

Super-antigens capable of augmenting growth in T cells are also within the scope of the invention. The term "super-antigen" as defined herein includes bacterial enterotoxins, or other bacterial proteins capable of stimulating proliferation of T cells. Super-antigens include staphylococcal enterotoxins, such as SEA, SEB, SEC, SED, and SEE, as well as antigens of viral or retroviral origin. Such other agents, either alone or in combination, may be identified by contacting the T cells with the agent(s), alone or together with another agent, and monitoring changes, preferably increases, in the marker protein level by, for example, Western blot analysis.

The term "T cell" is art-recognized and is intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a $CD4^+$ T cell, $CD8^+$ T cell, $CD4^+CD8^+$ T cell, $CD4^-CD8^-$ T cell, or any other subset of T cells.

The language "long term" T cell growth is intended to include rapid proliferation with an inhibited, or at least delayed, occurrence of cell death for a longer period of time or for more cell doublings than is currently possible using known methods of T cell activation. Cell death is intended to encompass cell death occurring by any mechanism. Cell death can be programmed cell death, also termed "apoptosis." Death of a T cell by apoptosis is characterized by features including condensation of nuclear heterochromatin, cell shrinkage, cytoplasmic condensation, and in a later stage of apoptosis, endonuclease mediated cleavage of the DNA of the T cell into discrete fragments. Upon electrophoretic analysis of the DNA of a cell in which apoptosis has occurred, a characteristic "ladder" of discrete DNA fragments is apparent.

The invention pertains to a system and methods for enhancing T cell growth, thereby protecting the T cells from cell death occurring naturally, or cell death resulting from an induced signal in the cell. "Rapid proliferation" in accordance with the present system and methods, refers to cell growth, or cell doublings (exponential growth), occurring at a more rapid rate as compared with a comparable population of untreated T cells, and at least relatively as quickly as would be achieved by current prior art T cell activation methods, but advantageously with at least a lower level of apoptosis. For example, in accordance with the present invention, $1 \times 10^6$ T cells can be expanded to at least $8.2 \times 10^9$ activated T cells in only three weeks of culture.

Apoptosis usually results from induction of a specific signal in the T cell. Thus, the system and method of the invention provides for protecting a T cell from cell death resulting from cross-linking of the T cell receptor (TCR) in the absence of a co-stimulatory signal. It is known in the art that presently cross-linking of the T cell receptor, either by a polyclonal activator, such as an anti-CD3 antibody and/or anti-CD28 antibody, or alternatively by an antigen on an antigen presenting cell (APC), in the absence of a co-stimulatory signal, results in T cell anergy or T cell death. Therefore, also including in the present invention is the enhanced long term T-cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

To ensure that the artificial antigen presenting cells (APCs) are universal (i.e., not limited HLA-matched T cells), a MHC-negative, genetically modified cell line was used. The myelogenous leukemia cell line K562 was chosen because it: (1) is of human origin; (2) lacks MHC class I and II molecules; (3) grows well using serum free medium, (4) has been extensively used in the literature (over 5700 references); (5) has been characterized cytogenetically; and (6) has been approved for other phase I clinical trails. Moreover, the K562 line used is free of mycoplasma and is adapted for growth in serum-free media. As a result, the resulting artificial APCs prepared in accordance with the present invention can be used 'off the shelf' to expand populations of $CD8^+$ T cells from any donor in a short time period, which is particularly advantageous in the setting of progressive malignancy.

Moreover, ex vivo activation of CTLs for adoptive immunotherapy circumvents the numerous defects in the function of DC that have been observed in cancer patients (Almand et al., *Clin. Cancer Res.* 6:1755-1766 (2000)). For comparison purposes a second genetically modified myeloid cell line, U937 was used as an artificial APC. Other such perpetual cell lines may be used as a basis for the artificial APC, depending on the nature of the T cells to be activated.

Effective immunotherapy will most likely require both $CD4^+$ and $CD8^+$ T cells, although the two are functionally distinct. The $CD4^+$ T cells act essentially as helper T cells, producing, e.g., cytokines; whereas the $CD8^+$ T cells are primarily killer cells. Therefore, it is not surprising that the growth characteristics of the two would be different. The $CD4^+$ T cells do not require the stimulation of the additional ligand to proliferate, whereas the $CD8^+$ T cells will not grow under the same conditions. However, upon exposure to the artificial APC of the present invention, the $CD8^+$ T cells proliferate as if they were $CD4^+$ T cells.

However, because the basic requirements for T cell growth include stimulation of the CD3/TCR receptor complex along with co-stimulation of CD28 to sustain longer term proliferation, both artificial APCs were stably transfected with the low affinity Fcγ receptor binding protein CD32 (K32/U32 cells). Transfection anchors the antibodies to the K562 or U937 cells because CD32 binds antibodies via their Fcγ receptor, antibodies will coat the surface of the APC cells in a manner similar to beads providing the requisite solid surface without the need for beads or other solid strata. Depending on the nature of the stimulatory agent, linkage can be performed by methods well known in the art. However, without such linkage the proteins in solution are unable to cross-link. If several agents are used for enhancing T cell growth, one or more agents may be in solution, while one or more agents may be linked to the APC. Accordingly, in the preferred embodiment, the thus-combined K562-CD32 cells (referred to herein as "K32 cells") or U937-CD32 cells (referred to a "U32 cells") were coated with anti-CD3 (aCD3; OKT3; Kung et al., *Science* 206:347-349 (1979)) and anti-CD28 (aCD28; 9.3; Hansen et al., *Immunogenetics* 10:247-260 (1980)) antibodies, and sorted for high expression, although despite multiple attempts, it was not possible to create U32 cells that had equivalent CD32 expression to the K32 cells.

Anti-CD32-FITC, anti-CD86-PE, anti-CD4 PE and isotype controls were purchased from Pharmingen (San Diego, Calif.). Cells were stained with the indicated antibodies at 4° C. and analyzed on a FACSCalibur (Mountain View, Calif.) after gating on live lymphocytes based on forward/side scatter and exclusion of To-Pro® (Molecular Probes, Eugene, OR) positive cells. Data was analyzed using FlowJo software (TreeSar, San Carlos, Calif.).

T cells were mixed with K32 cells or U32 cells at a ratio of 2:1, and anti-CD3, CD28 or MHC class I Ab were added at a concentration of 500 ng/ml. The 4-1BB ligand was also added to the preparation. Alternatively, for comparison purposes, CD3/MHC I or CD3/28 coated beads were mixed with T cells at a 3:1 ratio as previously described (Levine et al., 1997). Notably, for ex vivo expansion, altering the ratio of aAPC (K32) cells to T cells, or altering the amount of anti-CD3 Ab added to the aAPC may favor the expansion of TH1 v. TH2 cells. These alternative culture conditions may also favor the outgrowth of "regulatory" T cells, which are able to suppress T cell responses.

Typically, T cells were kept at a concentration of $5 \times 10^5$ and re-stimulated when the mean cell volume (as measured by Coulter Counter Multisizer II (Coulter, Hialeah, Fla.)) went below 250 fL. On average, the cells were re-stimulated every ten days. In some cases, 20 or 100 IU/ml IL-2 (Chiron, Emeryville, Calif.) was added to the cultures. Conditions appropriate for T cell culture include an appropriate media (e.g., Minimal Essential Media or RPMI Media 1640 (BioWhittaker)), which may contain factors necessary for proliferation and viability, including animal serum (e.g., fetal bovine or fetal calf serum, typically 0-10% (e.g., HyClone, Logan, UT)) 1 mM L-glutamine (BioWhittaker) and antibiotics (e.g., penicillin/streptomycin (Invitrogen). The T cells are maintained under conditions necessary to support growth, for example an appropriate temperature (e.g., 37° C.) and atmosphere (e.g., air plus 5% $CO_2$).

To maintain long term stimulation of a population of T cells following the initial activation and stimulation, it is necessary to separate the T cells from the activating stimulus (e.g., the anti-CD3 antibody) after a period of exposure. The T cells are maintained in contact with the co-stimulatory ligand throughout the culture term. The rate of T cell proliferation is monitored periodically (e.g., daily) by, for example, examining the size or measuring the volume of the T cells, such as with a Coulter Counter.

A resting T cell has a mean diameter of about 6.8 microns. Following the initial activation and stimulation and in the presence of the stimulating ligand, the T cell mean diameter will increase to over 12 microns by day 4, and begin to decrease by about day 6. When the mean T cell diameter decreases to approximately 8 microns, the T cells were reactivated and re-stimulated to induce further proliferation of the T cells. Alternatively, the rate of T cell proliferation and time for T cell re-stimulation can be monitored by assaying for the presence of cell surface molecules, such as B7-1, B7-2, which are induced on activated T cells.

For thymidine incorporation assays, cells were grown in 96 well plates and pulsed with 1 µCi/well of [$^3$H]-thymidine (Dupont NEN, Boston, Mass.) for 18 hours before harvest. Samples were run in triplicates. Cells were harvested with a Mach II 96 cell harvester (TomTec, Hamden, Conn.), and [$^3$H]-thymidine incorporation was measured in a 1205 Beta-plate liquid scintillation counter (Wallac Inc, Gaithersburg, Md.). For CFSE labeling (carboxy-fluorescein diacetate succinimidyl ester, Molecular Probes), CD4$^+$ T cells were washed 4× in PBS with $Ca^{++}$ and $Mg^{++}$ (BioWhittaker) and incubated with 3 µM CFSE for 8 minutes at room temperature. After labeling, cells were washed 3× in culture medium before stimulation. An unstimulated sample was kept as a control for the CFSE fluorescence intensity of undividing cells. Samples were analyzed every 6-24 hours on a FACSCalibur gating on live (forward/side scatter, To-Pro negative), CD4$^+$ cells.

Cytosolic RNA was purified using the RNeasy kit (Qiagen, Valencia, Calif.) and reverse transcribed using Roche 1$^{st}$ Strand cDNA synthesis kit (Roche, Basel, Switzerland). Primers and probes to detect IL-2, IL-15, B7-H3, B7-DC and 28S rRNA were designed using Primer Express software (PE Biosytems, Foster City, Calif.) and are available upon request. Real time PCR amplification and product detection was performed using the ABI Prism 7700 (PE Biosytems) as recommended by the manufacturer. Relative expression was determined by using the $\Delta\Delta Ct$ method according to the manufacturer's protocol and all results were normalized to 28S rRNA levels. The data is expressed as "fold induction" and was derived by dividing the relative expression of each experimental condition by the relative expression value obtained in resting CD4$^+$ or CD8$^+$ T cells or in resting K32 cells. A duplicate cDNA reaction was done in which the reverse transcriptase was left out of the reaction to detect the presence of genomic DNA. IL-2 contents in culture supernatants were assayed by ELISA (R&D Systems) according to the manufacturer's instructions. All values reported were assessed by using dilutions of culture supernatant that yielded read-outs within the linear portion of the standard curve.

In numerous experiments comparing K32 cells loaded with aCD3 and aCD28 antibodies to U32 cells or beads (e.g., 1:1 on M450 Dynal beads, Dynal, Lake Success, N.Y.; June et al, 1987) similarly loaded with aCD3 and aCD28 (CD3/28 beads), the K32 system has proven to be much more robust as a system for T cell expansion, having 2-4 more population doublings during a 10 day expansion period for a CD4$^+$ T cell population. One clear difference between the prior art bead method and the K32 cell method is the presence of adhesion and/or other co-stimulatory molecules (ICAM-1 and LFA-3) on the surface of the K562 cells. These serve to enhance the effects of the aCD3 and aCD28 antibodies and may transmit other co-stimulatory signals to promote T cell growth. Introduction of other co-stimulatory ligands, such as, CD80, CD86, OX40L, ICOS-L, ICAM, PD-L1 and PD-L2 by transfection or transduction may lead to the outgrowth of naive, memory, TH1, TH2, regulatory and/or regulatory T cell populations.

When the aCD3/aCD28 coated cells were used to stimulate CD8$^+$ T cell growth, the CD8$^+$ T cell population doubled six times (mean=6.0, SEM=1.6) in twenty (20) days, but absent the ligand, at the end of the culture the CD8$^+$ T cells become apoptopic, making them unusable for immuno-therapy. However, this limitation is overcome by using K32 cells transfected with a co-stimulator, preferably with the co-stimulator, 4-1BB ligand (4-1BBL), which provided long term growth for the CD8$^+$ T cells.

To confirm that 4-1BBL co-stimulation of human CD8$^+$ T cells in culture also prolonged their survival, human 4-1BBL were cloned and transfected into K32 cells. When K562-CD32-4-1BBL transfectants (also coated with anti-CD3 and anti-CD28 antibodies) were used to stimulate CD8$^+$ T cell growth, the CD8$^+$ T cell population doubled 13 times (mean=13.3, SEM =0.92). Moreover, the enhanced cell division provided by K562-CD32-4-1BBL APCs was shown to be dependent on 4-1BBL, since the response could be blocked in a dose-dependent fashion by the addition of soluble 4-1BBL-Ig chimeric protein. The difference in population doublings of T cells stimulated with 4-1BBL could not simply represent an initial increase in cell division during the first four days of culture, as determined by CFSE staining.

Stimulation by 4-1BBL significantly lowered the percentage of T cells undergoing early apoptosis after the first week of ex vivo culture (31% v. 3% at day 11 and 74% v. 22% at day 20). Furthermore, stimulation with K562-CD32-4-1BBL APCs was shown to rescue CD8$^+$ T cells from apoptosis that had been initially stimulated with K562-CD32 APCs, and these cells resumed growth for an additional two weeks. Thus, the previously described limitation relating to apoptosis of the TCR/CD28-stimulated growth of CD8$^+$ cells appears to reflect a requirement for co-stimulation, e.g., 4-1BBL signaling. As a result, the expansion of antigen-specific CTLs using this culture system, particularly by the use of appropriate co-stimulation that maintains effector functions, offers a promising advancement for immunotherapy.

However, the 4-1BBL did not necessarily enhance the growth rate of CD8$^+$ cells; rather, it prevented their apoptosis, making the CD8$^+$ cells suitable candidates for immunotherapy. In all experiments, the K562 artificial APCs were irradiated before stimulation of the cultures, and >95% of the live cells in the culture were CD8 positive within a week of K562 stimulation. Control cultures in which the anti-CD3 and anti-CD28 antibodies were left out demonstrated minimal (background) levels of [$^3$H]-thymidine, indicating that CD4$^+$ or CD8$^+$ T cells rather than the irradiated stimulator cells were responsible for the [$^3$H]-thymidine uptake (data not shown). Thus, the cell culture system of the present invention overcomes a major hurdle in the ability to use CD8$^+$ T cells for immunotherapy by allowing routine long term growth, making 4-1BBL a crucial component of both polyclonal and antigen specific CD8$^+$ infusions. Such mammalian-produced populations are referred to as "polyclonal" because the population comprises differing immunospecificities and antigen affinities.

By coating the K32 cells with only anti-CD3 and omitting anti-CD28, it was possible to screen for the presence of unknown co-stimulatory molecules by measuring CD4$^+$ T cell growth and IL-2 production. K32/CD3, U32/CD3 or CD3 coated artificial APCs were respectively used to stimulate freshly isolated CD4$^+$ T cells. T cell growth and IL-2 production were measured. Although only CD4$^+$ T cells stimulated with K32/CD3 exhibited high levels of [3H]thymidine incorporation, for the first 6 days after stimulation, CD4$^+$ T cells stimulated by K32/CD3 and K32/CD3/28 grew equivalently. But then the cells stimulated with K32/CD3 stopped expanding, whereas the cells stimulated by K32/CD3/28 kept growing.

The cells stimulated with anti-CD3 coated beads produced no detectable IL-2 in the supernatants, whereas CD4$^+$ T cells stimulated with K32/CD3 produced ng/ml levels of IL-2 after 3 days of culture. This stimulation, however, was unable to sustain IL-2 production, and after 5 days of culture it was undetectable in the supernatant. CD4$^+$ T cells stimulated with K32/CD3 returned to their resting cell size after one week (data not shown) and produced the lowest levels of IL-2. Likewise, the K32/CD3/28 and K32/86/CD3 stimulated cells produced intermediate levels of IL-2 and their cell volume returned to resting size after 10 days of culture.

Although K32/CD3/28 stimulated cells continued to grow exponentially for many days without re-stimulation, the U32/CD3/28 stimulated cells did not achieve log linear growth and resulted in only very modest T cell accumulation. Thus, the U32/CD3/28 artificial APC, despite initiating high levels of [$^3$H]-thymidine incorporation into CD4$^+$ T cells, were unable to sustain T cell growth, demonstrating that K32 cells were providing more than a scaffold for the anti-CD3/28 antibodies. Moreover, this indicates that the ability of cells to synthesize new DNA does not always correlate with sustained T cell expansion. To rule out that the inability of U32 cells to expand CD4 T cells was due to their lower level of CD32 expression, they were compared with an earlier generation of the K32 cells that had equivalent levels of CD32. However, as expected, the K32s expressing equivalent CD32 levels as the U32 cells were able to grow CD4$^+$ T cells, albeit slightly less effectively than the K32 cells having the highest levels of CD32. Accordingly, CD32 expression levels on U32 were not solely responsible for the differences in the ability to expand CD4$^+$ T cells.

Using CD4 T cells from three consecutive donors, the results consistently showed that K32/CD3/28 artificial APCs expanded the CD4$^+$ T cells more rapidly than the CD3/28 coated beads and were able to maintain exponential growth longer than cells stimulated with the CD3/28 coated beads. Nevertheless, CD4$^+$ T cells stimulated with K32/CD3/28 or K32/CD3/86 underwent on average at least two more population doublings within the first ten days of culture, indicating that it is a more rapid T cell expansion system than the CD3/28 coated beads. For example, to expand the CD4$^+$ T cells from one donor to clinically acceptable levels (1000-fold), the CD3/28 coated beads required 20 days of culture, whereas the K32/CD3/28 system required only 14 days (data not shown). Using CFSE labeling prior to stimulation, in cells assessed every 6 hours post stimulation, K32/CD3/28 stimulated CD4$^+$ T cells started dividing earlier than CD3/28-coated bead-stimulated CD4 T cells, showing a first division peak 44 hours (average of three experiments) after stimulation, whereas CD3/28 coated bead stimulated cells underwent the first division 51 hours of stimulation (data not shown). Moreover, the K32/CD3/28 stimulated cells divided in a more synchronized fashion.

Using fresh CD4$^+$ T cells, stimulated with either K32/CD3/28 or CD3/28 coated beads, and allowed to expand for 10 days, RNA was harvested three days after re-stimulation and cytokine production was measured by quantitative RT-PCR. It was observed that CD4$^+$ T cells re-stimulated with K32 CD3/28 could induce a wide array of cytokines (IL-2, IL-10, and IFNγ, a co-stimulatory molecule (ICOS) and a cell survival factor (Bcl-xL) in all cases in amounts≧cells stimulated with CD3/28 coated beads. As previously reported by Levine et al., *Int. Immunol.* 7:891-904 (1995), cells initially stimulated with immobilized anti-CD3 and CD28 antibodies can produce TH2 cytokines. However, upon re-stimulation these cells lose their ability to produce IL-4, and augment their expression of γIFN consistent with a TH1 phenotype.

The K32/CD3/28 artificial APCs are, therefore, more efficient at driving this TH1 cytokine profile in CD4$^+$ T cells than CD3/28 coated beads. Furthermore, log linear growth of CD4$^+$ T cells was maintained for at least 45 days (26 population doublings; 6.7×10$^7$ fold expansion, data not shown), demonstrating that K32 CD3/28 stimulated cells have the capacity to expand far beyond what is required for immunotherapy in clinical trials.

Nevertheless, for inducing long term stimulation of a population of CD4$^+$ or CD8$^+$ T cells, it may be necessary to reactivate and re-stimulate the T cells several times to produce a population increase of about 1,000-fold the original T cell population. Using this methodology, it is possible to get increases in a T cell population of from at least 100-fold to about 100,000-fold an original resting T cell population. Thus, these studies demonstrate that rapid expansion of CD4$^+$ T cells can be achieved using K32/CD3/28 artificial APCs and indicate that once these cells are infused back into the patient, they will be at least as functional as CD4+ T cells stimulated by CD3/28 coated beads (already tested in Phase I clinical trials wherein up to $3 \times 10^{10}$ autologous CD4 T cells were safely infused into HIV-1 infected individuals).

Large quantities of RNA-encoding MHC class I and II alleles linked to antigenic peptides are created in vitro using standard techniques, and subsequently introduced into K-32 cells. Once inside the cell, the RNA is translated and the encoded MHC molecule complexed with the specified peptide is transported to the cell surface. Advantageously, only T cells that recognize the MHC/peptide complex are activated, thus permitting the rapid expansion of antigen specific clones. Once characterized, these cell lines will be invaluable tools for immunotherapy, particularly since the cell lines permit the design of optimal co-stimulation regimes on a disease-by-disease basis. For example, the K32/4-1BBL/CD86 cells could be injected into a tumor and the K32 will uptake some tumor antigens and stimulate the T cells that recognize the tumor permitting eradication of the tumor.

A similar strategy could be used to identify tumor antigens. When lysed cells from a primary tumor are incubated with the K32/4-1BBL/CD86 cells and T cells from a MHC matched donor, the resulting expanded activated T cells will either recognize endogenous K562 antigens or antigens expressed on the tumor. When the resulting T cells are cloned using limiting dilution in the presence of anti-CD3-coated K32/4-BBL/CD86 cells, the resulting T cell populations can be initially tested to see if they recognize K32 cells or tumor. Those that recognize tumor can be further characterized to determine which antigen they recognize by sub-selection and/or library approaches. This method will then provide selected T cells that vigorously expand upon contact with the tumor antigen.

To practice the invention in vivo, a source of T cells is obtained from a subject. The term subject is intended to include living organisms in which an immune response can be elicited, e.g., mammals. Examples of subjects include humans, dogs, cats, mice, rats, and transgenic species thereof, although humans are preferred. T cells can be obtained from a number of sources, including peripheral blood leukocytes, bone marrow, lymph node tissue, spleen tissue, and tumors. Preferably, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through, e.g., a PERCOLL™ gradient.

A specific subpopulation of T cells, such as CD4+ or CD8+ T cells, can be further isolated by positive or negative selection techniques. For example, negative selection of a T cell population can be accomplished with a combination of antibodies directed to surface markers unique to the cells negatively selected. Preferably, as noted, is cell sorting via negative magnetic immunoadherence, which utilizes a cocktail of monoclonal antibodies directed to cell surface markers present on the cells negatively selected. For example, to isolate CD4+ cells, a monoclonal antibody cocktail typically includes antibodies to CD14, CD20, CD11b, CD16, HLA-DR, and CD8.

The process of negative selection results in an essentially homogenous population of CD4+ or CD8+ T cells. The T cells can be initially activated as described herein, such as by contact with a anti-CD3 antibody immobilized on a solid phase surface or an anti-CD2 antibody, or by contact with a protein kinase C activator (e.g., bryostatin) in conjunction with a calcium ionophore. To stimulate an accessory molecule on the surface of the T cells, a ligand is employed that binds the accessory molecule. For example, a population of CD4+ cells can be contacted with an anti-CD3 antibody and an anti-CD28 antibody, under conditions appropriate for stimulating proliferation of the T cells. Similarly, to stimulate proliferation of CD8+ T cells, an anti-CD3 antibody and a monoclonal antibody can be used, in conjunction with the second co-stimulatory agent, preferably as described, 4-1BBL.

T cells expanded by the system and methods of the invention together with the culture supernatant and cytokines can be administered to support the growth of cells in vivo. For example, in patients with tumors, T cells can be obtained from the individual, expanded in vitro and the resulting T cell population and supernatant can be re-administered to the patient to augment T cell growth in vivo.

The extent of cell viability and measured growth or proliferation in a population of cells can be determined for example by counting the number of T cells in both populations (before and after treatment or exposure) using a hemocytometer or a Coulter Counter. A preferred method for determining the extent of cell viability in a population of activated T cells is by propidium iodide exclusion assays, carried out by incubating the T cells with propidium iodide, a dye which is absorbed predominantly by dead cells and which is excluded from live (viable) cells. The extent of cell death is then determined by Fluorescence Activated Cell Sorter (FACS) analysis, using recognized methods in this art. Additional dyes that can be used include acridine orange and Hoechst 33342. Other methods for measuring the extent of cell viability in a population of T cells include end-labeling of cleaved DNA (e.g., Gavrieli et al., *J. Cell Biol.* 119:493 (1992)) and others techniques known in the art.

Another method for determining the extent of cell viability and growth in a population of T cells includes electrophoretic analysis of the nucleic acid of the T cells, wherein the nucleic acid of the T cells which can be in a purified or unpurified form is subjected to gel electrophoresis followed by staining of the gel with ethidium bromide and visualization of the nucleic acid under ultraviolet light. The nucleic acid from a population of T cells in which at least some of the T cells have undergone apoptosis will have the appearance of a "ladder," i.e., a population of discrete fragments of DNA. In contrast, DNA of T cells that have not undergone apoptosis will appear as a single high molecular weight band. Populations of T cells may be induced to undergo apoptosis when contacted with specific agents, such as those agents that cross-link the T cell receptor, e.g., an anti-CD3 antibody (aCD3), agents that cross-link Fas or the TNF receptor, and glucocorticoids.

The agents within the scope of the invention are preferably used in solution as described, but they may also be attached to a solid surface. The solid surface can be, for example, the surface of a tissue culture dish or a bead. Depending on the nature of the stimulatory agent, linkage to the solid surface can be performed by methods well known in the art. For example, proteins can be chemically cross-linked to the cell surface using commercially available cross-linking reagents (Pierce, Rockford Ill.) or immobilized on plastic by overnight incubation at 4° C. If several agents are used for enhancing T cell growth, one or more agents may be in solution, while one or more agents may be attached to a solid support.

Agents that act intracellularly to enhance T cell growth can be identified using standard assays. For example, T cells can be incubated in the presence or absence of a test agent which at different times can be measured by Western blot analysis, see, e.g., published PCT Application Number WO 95/00642, incorporated herein by reference. Thus, preferred agents for practicing the method of the invention include those that induce a significant increase in T-cell viability and growth, more preferably those that acts selectively, or at least preferentially, on T cells to augment growth and viability.

The language "nucleic acid molecule encoding a marker or co-stimulatory protein or agent" is intended to include any nucleic acid molecule that will be transcribed and translated into a T cell marker or protein that is directly increased in proportion to the increased cell proliferation achieved in accordance with the present invention upon introduction of the nucleic acid molecule into a T cell (e.g., the molecule can further contain appropriate control elements for regulating expression in the cell). Recognized T cell proliferation markers include, but are not limited to, Bcl-xL and IL-2 proteins. The nucleic acid molecule encoding marker or co-stimulatory protein can consist of only the coding region of the corresponding gene, or alternatively it can contain noncoding regions, such as 5' or 3' untranslated regions, introns, fragments thereof, or other sequences. The T cell marker protein is encoded by the marker gene.

The nucleic acid molecule can encode the full length marker or co-stimulatory protein or alternatively the nucleic acid can encode a peptidic fragment thereof that is sufficient to confer enhanced cell proliferation in accordance with the present invention, when introduced into the T cell. The nucleic acid can encode the natural marker or co-stimulatory protein or fragment thereof, or a modified form of the marker or co-stimulatory protein or fragment thereof. Modified forms of the natural marker or co-stimulatory protein that are within the scope of the invention are described below.

The invention is intended to include the use of fragments, mutants, or variants (e.g., modified forms) of the marker or co-stimulatory protein that retain the ability to enhance the proliferation of activated T cells. A "form of the protein" is intended to mean a protein that shares a significant homology with the natural marker or co-stimulatory protein and is capable of effecting enhanced activated T cell proliferation. The terms "biologically active" or "biologically active form of the protein," as used herein, are meant to include forms of marker or co-stimulatory proteins that are capable of effecting enhanced activated T cell proliferation. One skilled in the art can select such forms of marker or co-stimulatory protein based on their ability to enhance T cell proliferation upon introduction of a nucleic acid encoding the marker or co-stimulatory protein in the T cell. The ability of a specific form of marker or co-stimulatory protein to enhance T cell proliferation can be readily determined, for example, by comparing the modified cell with an untreated cell by any known assay or method, including many disclosed herein.

The nucleic acid can be a cDNA or alternatively it can be a genomic DNA fragment. Mutants of the marker or co-stimulatory protein can be prepared by a variety of known methods, such as, for example, by introducing nucleotide base pair modifications (e.g., substitutions, deletions, additions) to a nucleic acid molecule encoding the marker or co-stimulatory protein by standard methods, such as site-directed mutagenesis or polymerase chain reaction-mediated (PCR) mutagenesis. Preferred modifications include those that modify the half-life of the marker or co-stimulatory protein in the T cell (in some cases so that it is very short, in others very long).

Furthermore, it will be appreciated by those skilled in the art that changes in the primary amino acid sequence of the marker or co-stimulatory protein are likely to be tolerated without significantly impairing the ability of the protein to enhance T cell proliferation. Accordingly, mutant forms of the marker or co-stimulatory protein that have amino acid substitutions, deletions and/or additions as compared to the naturally occurring amino acid sequence of a comparable native the marker or co-stimulatory protein molecule, yet still retain the functional activity of the natural form of the marker or co-stimulatory protein as described herein are also encompassed by the invention. To retain the functional properties, preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta.-branched side chains (e.g., threonine, valine, isoleucine) and aromatic side chains (e.g., tyrosine, phenylalanine, tryptophan, histidine).

To express a nucleic acid molecule encoding a marker or co-stimulatory protein in a T cell such that the level of recognized markers, such as Bcl-xL or IL-2 protein, is increased in the T cell in direct relationship with increased cell proliferation, the nucleic acid must be operably linked to regulatory elements. "Operably linked" is intended to mean that the nucleotide sequence encoding the marker or co-stimulatory protein is linked to at least one regulatory sequence in a manner which allows expression of the nucleotide sequence in the T cell. Regulatory sequences are selected to direct expression of the desired protein in an appropriate T cell. Accordingly, the term "regulatory sequence" includes promoters, enhancers and other expression control elements. Such regulatory sequences are known to those skilled in the art and are further described in Goeddel, *Gene Expression Technology: Methods in Enzymology* 185, Academic Press, San Diego, Calif. (1990).

These regulatory elements include those required for transcription and translation of the nucleic acid encoding the marker(s) or co-stimulatory protein(s), and may include promoters, enhancers, polyadenylation signals, and sequences necessary for transport of the molecule to the appropriate cellular compartment, which is preferably the outer mitochondrial membrane (Gonzales-Garcia et al., *Development* 120:3033 (1994)). When the nucleic acid is a cDNA in a recombinant expression vector, the regulatory functions responsible for transcription and/or translation of the cDNA are often provided by viral sequences. Examples of commonly used viral promoters include those derived from polyoma, adenovirus 2, cytomegalovirus and simian virus 40, and retroviral LTRs.

Regulatory sequences linked to the cDNA can be selected to provide constitutive or inducible transcription. Inducible transcription can be accomplished by, for example, use of an inducible enhancer. Thus, in a specific embodiment of the invention the nucleic acid molecule encoding the T cell marker or co-stimulatory protein is under the control of an inducible control element such that expression of the marker or co-stimulatory protein can be turned 'on' or 'off' (or intermediate levels in between) using an agent which affects the inducible control element (e.g., expression can be modulated by modulating the concentration of the inducing agent in the presence of the T cell). This allows for switching 'on' or 'off' of the protective effect of the marker or co-stimulatory protein against cell death in the T cells, or the systems necessary for the enhanced proliferation of the T cells.

It may, indeed, be desirable to promote T cell survival only in certain conditions or only for a certain amount of time. For example, at the site of an infection in a subject, it may be desirable to boost the immune reaction to eliminate the infectious agent in a limited time frame until clinical levels of activated T cells can be added. However, upon clearance of the infectious agent it may be desirable to eliminate the added T cells. Thus, the expression of marker or co-stimulatory proteins in the T cells located at the site of an infection can be stimulated through the inducible control element by contacting the T cells with the inducing agent. Then, upon clearance of the infection, inducing agent can be removed to stop production of the marker or co-stimulatory protein in the T cells. Such controllable inducible regulatory systems for use in mammalian cells are known in the art.

The inducible control elements may function in all T cells, or alternatively, only in a specific subset of T cells, such as in $CD4^+$ T cells, $CD8^+$ T cells, T helper 1 (Th1), T helper 2 (Th2) cells. Inducible control elements can also be selected which are regulated by one agent in one type of T cells (such as $CD4^+$ T cells) yet which are regulated by another agent in another type of T cells (such as $CD8^+$ T cells).

In another embodiment of the invention, the nucleic acid molecule encoding a marker or co-stimulatory protein for enhanced T cell proliferation is under the control of regulatory sequences which constitutively drive the expression of the nucleic acid molecule. In a specific embodiment of the invention, T cells from a subject infected with HIV are modified to constitutively express proteins associated with enhanced T cell proliferation. Regulatory elements which drive constitutive expression of nucleic acid molecules to which they are operably linked are preferably viral promoters. Examples of commonly used viral promoters include those derived from polyoma, adenovirus 2, cytomegalovirus and simian virus 40, and retroviral LTRs. Alternatively, T cell-specific enhancers can be used, e.g., T cell receptor enhancers (see, e.g., Winoto et al., *EMBO J.* 8:729-733 (1989)).

When the nucleic acid molecule encoding a marker or co-stimulatory protein is operably linked to regulatory elements it is typically carried in a vector. Examples of vectors include plasmids, viruses or other nucleic acid molecules comprising, for example, sequences that are necessary for selection and amplification of the nucleic acid molecule in bacteria. Thus, a nucleic acid molecule comprising a nucleotide sequence encoding a marker or co-stimulatory protein operably linked to regulatory control elements, is also referred to herein as an "expression vector." Vectors, e.g., viral vectors, are further discussed below.

The nucleic acid molecule encoding a marker or co-stimulatory protein can be introduced into the T cell by various methods typically referred to as transfection. The terms "transfection" or "transfected with" refers to the introduction of exogenous nucleic acid into a mammalian cell and are intended to encompass a variety of techniques useful for introduction of nucleic acids into mammalian cells, including electroporation, calcium-phosphate precipitation, DEAE-dextran treatment, lipofection, microinjection, and viral infection. Suitable methods for transfecting mammalian cells can be found in Sambrook et al. (*Molecular Cloning: A Laboratory Manual*. $2^{nd}$ Edition. Cold Spring Harbor Laboratory press (1989)) and other laboratory textbooks. Transfection may also be used in the preparing the artificial APC to link the ligand to the basic cell line.

In a preferred embodiment of the invention, the nucleic acid molecule encoding a marker or co-stimulatory protein is introduced into a T cell by using a viral vector. Such viral vectors include, for example, recombinant retroviruses, adenovirus, adeno-associated virus, and herpes simplex virus-1. Retrovirus vectors and adeno-associated virus vectors are generally considered to be the recombinant gene delivery system of choice for the transfer of exogenous genes in vivo, particularly into humans. Alternatively, such vectors can also be used for introducing exogenous genes ex vivo into T cells. These vectors provide efficient delivery of genes into T cells, and the transferred nucleic acids are stably integrated into the chromosomal DNA of the host cell.

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, *Blood* 76:271 (1990)). Thus, recombinant retrovirus can be constructed in which part of the retroviral coding sequence (gag, pol, env) has been replaced by nucleic acid encoding a marker or co-stimulatory protein, rendering the retrovirus replication defective. This is a consideration when using the tumor cell line K567 in the present invention. The replication defective retrovirus is then packaged into virions that can be used to infect a target cell through the use of a helper virus by standard techniques. Protocols for producing recombinant retroviruses and for infecting cells in vitro or in vivo with such viruses can be found in *Current Protocols in Molecular Biology*, Ausubel et al. (eds.) Greene Publishing Associates, (1989), Sections 9.10-9.14 and other standard laboratory manuals.

Examples of suitable retroviruses include pLJ, pZIP, pWE and pEM that are well known to those skilled in the art. Examples of suitable packaging virus lines for preparing both ecotropic and amphotropic retroviral systems are also known.

In another embodiment of the invention, the nucleic acid molecule encoding a marker or co-stimulatory protein is delivered into a specific cell in the form of a soluble molecular complex. The complex contains the nucleic acid releasably bound to a carrier comprised of a nucleic acid binding agent and a cell-specific binding agent which binds to a surface molecule of the specific cell and is of a size that can be subsequently internalized by the cell. Such complexes are described in U.S. Pat. No. 5,166,320. In another embodiment of the invention the nucleic acid encoding marker or co-stimulatory protein is introduced into T cells by particle bombardment, as described in Yang et al., *Nature Medicine* 1:481 (1995)).

In one embodiment, the method of the invention involves enhancing the proliferation of a population of T cells by contacting the T cell with at least one agent that increases Bcl-xL or IL-2 protein ("marker") level in the T cell in conjunction with enhanced proliferation. In a preferred embodiment of the invention, the at least one agent which interacts with the T cell to increase the level of marker protein level includes one or more agents which interact with molecules on the surface of the T cell, such as the T cell receptor and CD3 or CD28. In another embodiment of the invention, the at least one agent acts intracellularly, for example by increasing expression of the marker gene. The language "an agent which acts intracellularly to augment marker protein level in the T cell" is intended to include agents which do not bind to a surface receptor on the T cell, but rather mimic or induce an intracellular signal (e.g., second messenger) transduced from cross-linking a receptor on the T cell which results in augmentation of the marker protein level in the T cell and enhanced proliferation. The agent may stimulate the production of the necessary proteins in the T cell through various mechanisms, such as by increasing transcription of the marker gene, stabilizing marker mRNA, or by increasing translation of marker mRNA.

In another embodiment of the invention, proliferation of the T cell population is enhanced by methods comprising contacting the T cell or APC with a marker or co-stimulatory protein in a form suitable for uptake by the cell. Thus, in a specific embodiment of the invention, a marker or co-stimulatory protein is synthesized in vitro by conventional techniques, such as in a bacterial expression system, and then delivered to the APC or to the T cell in a suitable vehicle. Suitable vehicles include liposomes that can be modified to target specific cells, in particular T cells, or a selective subset of T cells.

The marker or co-stimulatory protein can be produced in vivo or in vitro by inserting a nucleic acid molecule encoding the marker or co-stimulatory protein or a biologically active form of same into various expression vectors, which in turn direct the synthesis of the corresponding protein in a variety of hosts, preferably eucaryotic cells, such as mammalian or insect cell culture, but also procaryotic cells, such as E. coli.

Expression vectors within the scope of the invention comprise a nucleic acid as described herein and a promoter operably linked to the nucleic acid. Such expression vectors can be used to transfect host cells to thereby produce the protein encoded by the nucleic acid as described herein. An expression vector of the invention, as described herein, typically includes nucleotide sequences encoding a marker or co-stimulatory protein operably linked to at least one regulatory sequence.

As regulatory sequences have been described above, it should be understood that the design of the expression vector may depend on such factors as the choice of the host cell to be transfected, e.g., a cell line for use as an APC or a T cell, and/or the type and/or amount of protein desired to be expressed.

An expression vector of the invention can be used to transfect cells, either procaryotic or eucaryotic (e.g., mammalian, insect or yeast cells) to thereby produce proteins encoded by nucleotide sequences of the vector. Expression in procaryotes is most often carried out in E. coli with vectors containing constitutive or inducible promoters. Certain E. coli expression vectors (so called fusion-vectors) are designed to add a number of amino acid residues to the expressed recombinant protein, usually to the amino terminus of the expressed protein. These are well known in the art and commercially available.

One strategy to maximize expression of a marker or co-stimulatory protein in E. coli is to express the protein in a host bacteria with an impaired capacity to proteolytically cleave the recombinant protein (Gottesman, in *Gene Expression Technology: Methods in Enzymology* 185, Academic Press, (San Diego, Calif.) 119-128 (1990)). Another strategy would be to alter the nucleotide sequence of the nucleic acid molecule encoding the marker or co-stimulatory protein to be inserted into an expression vector so that the individual codons for each amino acid would be those preferentially utilized in highly expressed E. coli proteins (Wada et al., *Nuc. Acids Res.* 20:2111-2118 (1992)). Such alteration of nucleic acid sequences are encompassed by the invention and can be carried out by standard DNA synthesis techniques.

Alternatively, a marker or co-stimulatory protein can be expressed in a eucaryotic host cell, such as a mammalian cell (e.g., Chinese hamster ovary cells (CHO) or NSO cells), insect cells (e.g., using a baculovirus vector) or yeast cells. Other suitable host cells may be found in Goeddel, (1990), or are known to those skilled in the art. Eucaryotic, rather than procaryotic, expression of a marker or co-stimulatory protein may be preferable since expression of eucaryotic proteins in eucaryotic cells can lead to partial or complete glycosylation and/or formation of relevant inter- or intra-chain disulfide bonds of a recombinant protein. For expression in mammalian cells, the expression vector's control functions are often provided by viral material. For example, commonly used promoters are derived from polyoma, adenovirus 2, cytomegalovirus and simian Virus 40. A preferred cell line for production of recombinant protein in this case is the K567 myeloma cell line available from ATCC.

For stable transfection of mammalian cells, it is known that, depending upon the expression vector and transfection technique used, only a small faction of cells may integrate DNA into their genomes. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same plasmid as the gene of interest or may be introduced on a separate plasmid. Cells containing the gene of interest can be identified by drug selection (e.g., cells that have incorporated the selectable marker gene will survive, while the other cells die). The surviving cells can then be screened for production of, for example, a marker protein by, e.g., immunoprecipitation from cell supernatant with an anti-marker antibody.

Marker or co-stimulatory proteins produced by recombinant technique may be secreted and isolated from a mixture of cells and medium containing the protein. For secretion of marker or co-stimulatory protein or other necessary protein for enhanced T cell proliferation, a DNA sequence encoding an appropriate signal peptide is linked to the 5' end of the nucleotide sequence encoding the marker or co-stimulatory protein, such that it is linked to the signal peptide that will result in secretion of the protein from the cell. Alternatively, the protein may be retained cytoplasmically and the cells harvested, lysed and the protein isolated. A cell culture typically includes host cells, media and other byproducts. Suitable mediums for cell culture are well known in the art. Protein can be isolated from cell culture medium, host cells, or both using techniques known in the art for purifying proteins.

The recombinantly produced marker or co-stimulatory protein can then be packaged in a suitable pharmaceutical vehicle for administration into a subject for enhanced T cell proliferation, or for introduction in the preparation of the APC cell, or for preparation of an enhanced number of the activated T cells ex vivo. For in vivo and ex vivo introduction into the T cells of the recombinant marker or co-stimulatory protein or other necessary protein for enhanced T cell proliferation, the recombinant protein is preferable packaged in liposomes. However other carrier systems can be used.

For treating human cells, the enhanced T cells are preferably of human origin although T cells from other animal species are also encompassed by the invention. Moreover, the enhanced T cells can be used across species, as long as the T cell growth and viability is enhanced to permit the rapid production of polyclonal or antigen specific T cells, while apoptosis of such cells is significantly reduced.

The term "subject" is intended to include living organisms in which an immune response can be elicited using the activated T cells of the present invention, e.g., mammals.

Examples of subjects include humans, dogs, cats, mice, rats, and transgenic species thereof. For example, animals within the scope of the invention include animals of agricultural interest, such as livestock and fowl. Alternatively, the methods of the invention can also be applied to plants. For practicing the methods of the invention in vivo, the agents are administered to the subjects in a biologically compatible form suitable for pharmaceutical administration in vivo. By "biologically compatible form suitable for administration in vivo" is meant, e.g., activated T cells prepared using the APC of the present invention, to be administered in which any toxic effects are outweighed by the therapeutic effects of the treatment. Agents to be administered include nucleic acid molecules encoding marker or co-stimulatory proteins or other proteins necessary for the enhanced proliferation of the T cells or encoding antisense nucleic acid molecules to inhibit production of same in the cell. Also included are agents that act intracellularly to augment or reduce levels of activated T cells, or marker or co-stimulatory proteins or other proteins necessary for the enhanced proliferation of the T cells, and agents which regulate an inducible control element operably linked to a nucleic acid molecule encoding same, or operably linked to a nucleic acid molecule encoding antisense nucleic acid molecules of same.

Administration of a therapeutically active amount of the activated T cells of the present invention is defined as an amount effective, at dosages and for periods of time necessary to achieve the desired result. For example, a therapeutically active amount of activated T cells that have been enhanced by the present invention may vary according to factors such as the disease state, age, sex, and weight of the subject, and the ability of the agent to elicit a desired response in the subject. Dosage regimens to return the thus-activated T cells to the patient may be adjusted to provide the optimum therapeutic response. For example, several divided doses may be administered daily or the dose may be proportionally reduced as indicated by the exigencies of the therapeutic situation.

The thus-activated cells may be administered to the patient in a convenient manner, such as by injection (subcutaneous, intravenous, etc.), oral administration, inhalation, transdermal application, or rectal administration, depending on the route of administration. Pharmaceutical compositions suitable for injectable use include sterile aqueous solutions (where water soluble) or dispersions and sterile powders for the extemporaneous preparation of sterile injectable solutions or dispersion. In all cases, the composition must be sterile, and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the activated T cells in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the activated T cells prepared in accordance with the present invention and the particular therapeutic effect to be achieved, and (b) the limitations inherent in the art of compounding such T cells for the treatment of sensitivity in subjects.

The invention pertains to a system and methods for enhancing T cell proliferation by methods that can be practiced either in vivo or ex vivo. When practiced ex vivo, peripheral blood mononuclear cells can be obtained from a subject and isolated by, e.g., density gradient centrifugation, e.g., Ficoll/Hypaque. In a specific embodiment, the purified peripheral blood cells are then contacted with an agent that modulates activated T cell proliferation. In other embodiments of the invention, the peripheral blood mononuclear cells are further enriched in specific cell types prior to being contacted with the co-stimulatory agent. Monocytes can be depleted, for example, by adherence on plastic. If desired, the selected T cell population can, depending on the selected population of cells, be further enriched by separation from residual monocytes, B cells, NK cells, $CD4^+$ or $CD8^+$ T cells using monoclonal antibody (mAb) and anti-mouse-Ig coated magnetic beads using commercially available mAbs (such as anti-CD14 (Mo2), anti-CD11b (Mo1), anti-CD20 (B1), anti-CD16 (3G8) and anti-CD8 (7PT 3F9) mAbs). The invention can also be applied to subsets of $CD4^+$ T cells, such as $CD4^+$ $CD45RA^+$ (naive $CD4^+$ T cells) and $CD4^+$ $CD45RO^+$ (memory T cells) T cell subsets. These can be prepared as described above, with the additional use of anti-CD45RO antibody (UCHLI) for the preparation of the $CD4^+$ $CD45RA^+$ cells and the addition of anti-CD45RA antibody (2H4) for the preparation of the $CD4^+$ $CD45RO^+$ T cells.

The efficiency of the purification can be analyzed by flow cytometry (Coulter, EPICS Elite), using e.g., anti-CD3, anti-CD4, anti-CD8, anti-CD14 mAbs, or additional antibodies that recognize specific subsets of T cells, followed by fluorescein isothiocyanate conjugated goat anti mouse immunoglobulin (Fisher, Pittsburgh, Pa.) or another secondary antibody.

The type of cell population used in vivo will depend on various factors including the type of agent(s) used for modulating T cell proliferation, the type of vehicle used to deliver the agent(s) to the T cells, and the subset of T cells in which it is desirable to augment proliferation. Thus, when an agent specifically affects a subset of T cells (e.g., by use of a delivery vehicle that targets only a specific subset of T cells)

purification of the specific subset of T cells is not required. Vehicles that allow targeting of the agent to specific subsets of cells include liposomes or recombinant viral particles to which molecules that specifically recognize the desired cell type are linked. Such molecules include antibodies to surface molecules or ligands to receptors. If only a selective subset of T cells is desired to be targeted, e.g., $CD4^+$ T cells, and the agent used is not capable of targeting selectively this subset of T cells, it may be necessary to isolate the specific subset of T cells prior to contacting the cells with the co-stimulatory agent.

The amount of co-stimulatory agent will depend on various factors, such as the type of agent, the effect desired, and the population of cells contacted with the agent. The appropriate amount of agent to be added to the population of cells can be determined by performing assays in which various doses of agent are added to the cell culture and the amount of co-stimulatory agent is determined at various time points by various analyses, as described herein. If a heterologous population of cells is contacted with the agent, it may be necessary to first isolate the subset of T cells in which cell proliferation is desired prior to subjecting the cells to analyses or cell count. Specific subsets of T cells can be isolated from a population of cells by negative selection, as described above, or alternatively a specific subset of T cells can be isolated by using FACS.

Alternatively, the method of the invention can be practiced in vivo or ex vivo, as defined in applicants' co-pending application U.S. Ser. No. 10/336,224.

In a preferred embodiment, the method of the invention is used in vivo for preventing cell death of $CD4^+$ T cells of an HIV infected individual, and for protecting T cells from HIV infection. During HIV infection, the virus infects and kills $CD4^+$ T cells. Thus, the number of $CD4^+$ T cells in the infected individual progressively decreases to numbers insufficient for preventing infection of the subject by microorganisms. Thus, increasing the level of activated T cells in the individual by reintroducing into the individual populations of ex vivo activated T cells, provides a therapeutic response to HIV-induced cell death. Moreover, the method of the invention may directly result in an expression of increased numbers of $CD4^+$ T cells in an HIV infected subject, and/or a reduced rate of T cell depletion in such an individual.

In one embodiment of the invention expansion is provided ex vivo for a population of T cells from an individual having a T cell associated disorder, such as an infection with HIV, or other infectious agent that renders the T cells susceptible to apoptosis. The expanded T cell population can then be administered back to the subject in vivo. In a preferred embodiment, the T cells are stimulated ex vivo with a combination of agents providing a primary activation signal and an agent which provides a co-stimulatory signal to the T cell. In a more preferred embodiment, the T cells are cultured with a combination of an agent that interacts with CD28 on the T cell and an agent that stimulates the T cells through the T cell receptor, such that T cell growth is enhanced and the cells are protected from cell death.

In another embodiment, the T cells of a subject, e.g., a subject infected with HIV, are enhanced by combining the ex vivo system and methods described above with in vivo methods. The system and methods can also comprise contacting the $CD4^+$ T cell, $CD8^+$ T cell, or other T cell populations of the individual in vivo and/or ex vivo with one or more agents that augment T cell production. Then, the thus-activated T cells are administered to the patient (autologously or allogenically).

Alternatively, the invention is useful for boosting an immune reaction to more rapidly eliminate an infection or a cancer. Thus, in a specific embodiment, activated $CD4^+$, $CD8^+$, or other T cell populations are produced in clinically useful quantities and used to supplement those of the infected individual in vivo. Thus, e.g., the additional activated helper T cells will provide more "help" to more effector cells than the reduced number of T helper cells would normally be able to provide in the infected individual. Similarly, a $CD4^+$ and/or $CD8^+$ T cell having an extended life span will be able to lyse more target cells than such T cells with a normal life span. Thus, methods within the scope of the invention comprise methods for treating systemic infections and local infections in a patient. Accordingly, the thus-activated T cells can be administered in vivo systemically or locally following ex vivo or in vitro activation. In an even more preferred embodiment of the invention, the co-stimulatory agent is an agent which has a short half-time, such that the life span of the activated T cell is not prolonged for times longer than necessary (e.g. the activated T cell becomes a memory T cell or dies following clearance of the infection).

One possible use of in vivo expanded polyclonal T cells is to reconstitute the immune system of patients infected by any disease or condition that can be modulated or eliminated by the addition of quantities of activated T cells. Such diseases and conditions are well known in the art, and may include, but are not limited to, infections, cancers, particularly cancerous tumors, or systemic allergic responses or immunodeficiency syndromes or conditions. However, for this therapy to be successful, gaps in the T cell repertoire must not be created by selective expansion of certain T cell subtypes.

In a specific embodiment, the method of the invention is used for treating an autoimmune disease in a subject, although treatment of any of a variety of cancers in a subject could also be provided. Susceptibility to cell death is increased in autoreactive T cells to ameliorate the effects of the autoimmune disease. Examples of autoimmune diseases which may be treated include, for example, but without limitation, multiple sclerosis, insulin dependent diabetes mellitus, arthritis (e.g., rheumatoid arthritis, juvenile rheumatoid arthritis, osteoarthritis), myesthenia gravis, myocarditis, Guillan-Barre Syndrome, systemic lupus erythematosis, autoimmune thyroiditis, dermatitis, psoriasis, Sjogren's Syndrome, alopecia areata, Crohn's disease, aphthous ulcer, iritis, conjunctivitis, keratoconjunctivitis, ulcerative colitis, allergy, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, and interstitial lung fibrosis. In another embodiment, the method of the invention is used to reduce graft rejection. The method can further comprise administering to the host an agent that blocks co-stimulation of the T cells, such as CTLA4Ig.

The present invention is further described in the following examples. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims. Thus, the invention should in no way be construed as being limited to the following example, but rather, should be construed to encompass any and all variations that become evident as a result of the teaching provided herein.

EXAMPLES

Protocols

The constructions described below are carried out according to the general techniques of genetic engineering and molecular cloning detailed in, e.g., Maniatis et al., (*Laboratory Manual*, Cold Spring Harbor, Laboratory Press, Cold Spring Harbor, N.Y. (1989)). The steps of PCR amplification follow known protocols, as described in, e.g., *PCR Protocols—A Guide to Methods and Applications* (ed., Innis, Gelfand, Sninsky and White, Academic Press Inc. (1990)). Notably, the oligonucleotides used to modify the Ad genome may use different restriction enzyme sites than those identified below, and may use a slightly different insertion site in the genome, without affecting the outcome of the invention. Such variations, so long as not substantial, are within the understanding of one of ordinary skill in the art.

Moreover, cells are transfected according to standard techniques, well known to a person skilled in the art. Protocols enabling a nucleic acid to be introduced into a cell may employ known methods, e.g., calcium phosphate transfection (Maniatis et al., 1989), DEAE-dextran techniques, electroporation, methods based on osmotic shocks, micro-injection of the selected cell, or methods based on the use of liposomes.

Cloning and construction of cell-based artificial APC (aAPC). human CD32 was cloned from neutrophils into the pcDNA 3.1 neo vector (Invitrogen, Carlsbad, Calif.), and transfected into K562 cells (American Type Culture Collection, Manassas, Va.) by electroporation; K32 cells were cloned by FACS sorting. Similarly, (h)4-1BB ligand was cloned from B cells into the pcDNA3.1 hygro vector (Invitrogen), and transfected into K32 cells before FACS sorting.

$CD8^+$ T lymphocyte preparation and K562 cell culture. Fresh peripheral blood lymphocytes were obtained by leukopheresis and elutriation. $CD4^+$ T cells were purified by negative selection using the OKT4 Ab (ATCC) as described by June et al., *Mol. Cell Biol.* 7:4472-4481 (1987). (Ab=antibodies; mAb=monoclonal antibodies). $CD8^+$ T cells were purified identically, but OKT8 Ab (ATCC) was substituted for the OKT4 Ab. All cultures were maintained in AIM V (GIBCO BRL, Life Technologies, Grand Island, N.Y.) with 3% human AB serum (BioWhittaker, Walkersville, Md.). Human IL-2 (Chiron Therapeutics, Emeryville, Calif.) was added at 20 IU/mL where indicated.

T lymphocyte stimulation and long-term culture. At each time point at which the lymphocytes were stimulated, the K562 cell-based aAPCs were irradiated with 10,000 rads, then washed twice into T cell culture medium. Cell-based aAPCs were then loaded with anti-CD3 (OKT3) and anti-CD28 mAbs (9.3) at 0.5 µg/ml for 10 minutes at room temperature. Unwashed, antibody-loaded aAPCs were then mixed with $CD8^+$ T cells at a 1:2 K562:T cell ratio. The T cell concentration was maintained at $0.5 \times 10^6$ cells/ml throughout culture, and up to $100 \times 10^6$ T cells were maintained in flasks. Anti-CD3/28 bead stimulation was performed as previously described by Levine et al., *J. Immunol.* 159:5921-5930 (1997). Cultured T cells were monitored for cell volume and enumerated on a Coulter Multisizer II (Miami, Fla.) every 23 days, and re-stimulated at 7-10 day intervals when the mean lymphocyte volume reached 200-250 fL.

Flow cytometry and FACS sorting. Cells were stained with antibodies (and/or MHC tetramers) at 4° C., and analyzed on a FACSCalibur (BD BioSciences, Mountain View, Calif.). Apoptosis assays were conducted per the manufacturer's protocol (R & D Systems, Minneapolis, Minn.). Cell sorting was performed on a MoFlo cell sorter (Cytomation, Fort Collins, Calif.). All flow cytometry data were analyzed with FlowJo software (TreeStar, San Carlos, Calif.).

Real-time PCR and TCR Vβ repertoire analysis. Real time PCR was performed and normalized to 28s rRNA levels as described previously by Riley et al., *J. Immunol.* 166, 4943-4948 (2001). The diversity of TCR Vβ repertoire was assessed by determination of CDR3 size lengths by multiplex PCR as previously described by Claret et al., *J. Clin. Invest.* 100:855-866 (1997).

$^{51}$Cr release assays. Target T2 cells (ATCC) were pulsed with 10 µM flu peptide (see Maus et al., 2002) or left unpulsed before labeling with $^{51}$chromium (PerkinElmer Life Sciences, Inc., Boston Mass.). After a four-hour incubation of effectors with targets, radioactivity was counted from an aliquot of supernatant. Specific lysis was calculated by standard methods.

After a four-hour incubation of effectors with targets, radioactivity was counted from an aliquot of supernatant. Specific lysis was calculated by standard methods.

Example 1

Construction of Artificial APCs (aAPCs)

To test the hypothesis that $CD8^+$ T cells have distinct co-stimulation requirements for long-term growth, a cell-based aAPC was designed which could be genetically manipulated to express different co-stimulatory molecules in addition to CD28. K562 cells were chosen because they do not express HLA proteins that would promote allogeneic responses, but they do express the T cell interaction molecules ICAM (CD54) and LFA-3 (CD58) (FIG. 1A). Also, the eventual introduction of irradiated K562 cells into the clinical setting can be expedited because these cells are easily killed by natural killer (NK) cells and are propagated in serum-free medium. K562 cells expressing the human Fcγ receptor CD32 (K32 cells) were transfected and then cloned to permit exogenous loading of anti-CD3 and anti-CD28 antibodies (FIG. 1A). Similarly, the K32/4-1BBL line (FIGS. 1A, B) was generated by transfecting K32 cells with human 4-1BB ligand. Cultures were initiated by adding γ-irradiated aAPCs to fresh human $CD8^+$ T cells prepared by negative selection as described.

Figure 1C:
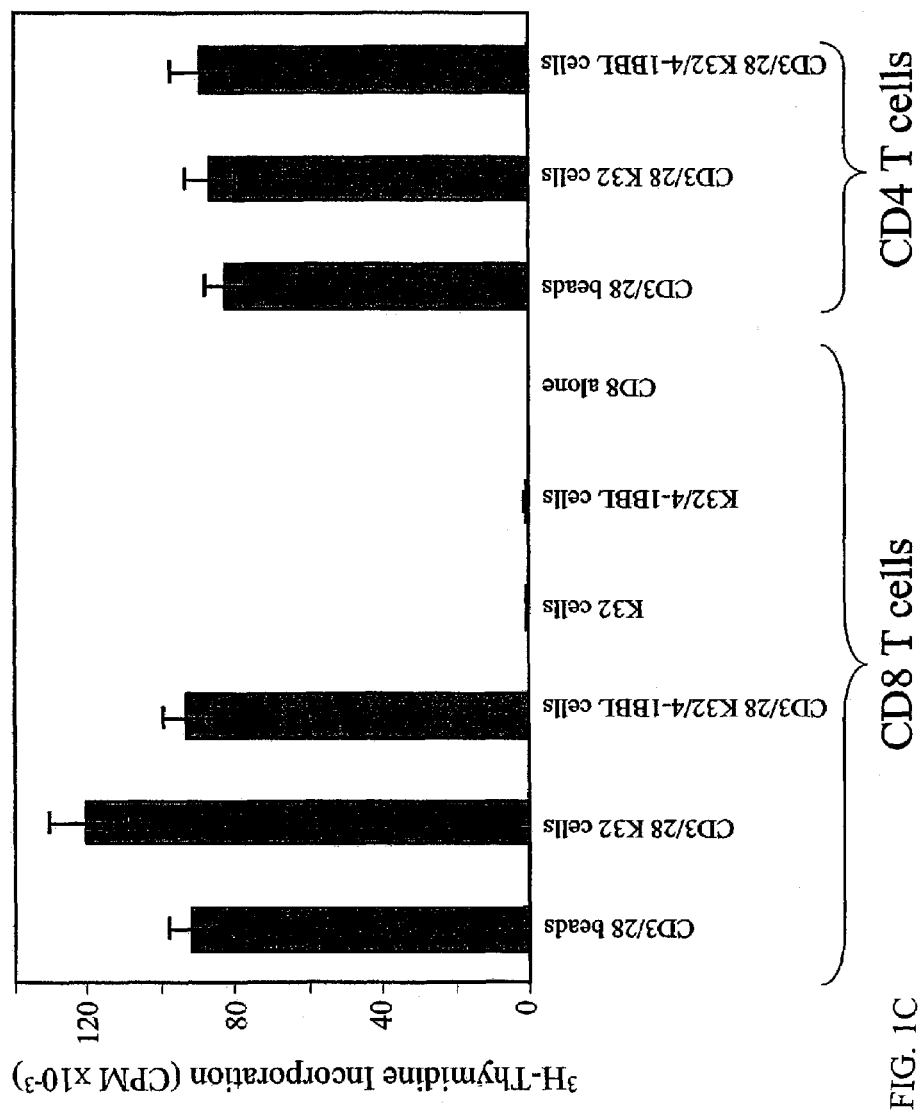

K32 and K32/4-1BBL aAPCs efficiently activate human polyclonal $CD8^+$ T cells. The aAPCs were tested for their ability to stimulate the initial activation and proliferation of primary $CD8^+$ T cells. The T cells were stimulated with three different preparations of aAPCs: CD3/28 beads, K32 cells coated with anti-CD3 and anti-CD28 (K32/CD3/28), or K32/4-1BBL cells coated with the same antibodies (K32/4-1BBL/CD3/28). The initial rate of growth of the T cells stimulated with all three aAPCs was equivalent, as judged by thymidine incorporation (FIG. 1C). This observation was confirmed by labeling fresh T cells with carboxyfluorescein diacetate succinimidyl ester (CFSE) and tracking cell division during the first five days of culture (data not shown). The K562 cell-based system was found to be equivalent to CD3/28 beads for the induction of proliferation and cell division of $CD4^+$ T cells (FIG. 1C and data not shown). Neither K562-based aAPCs, nor $CD8^+$ T cells, nor $CD4^+$ T cells incubated separately showed any proliferation (FIG. 1C and data not shown). Thus, the requirements for the initial rounds of $CD8^+$ T cell proliferation were satisfied equally by CD3/CD28 stimulation provided in the context of polystyrene beads or cell based aAPCs, and the addition of 4-1BBL costimulation did not appear to have further benefit.

Example 2

K32/4-1BBL aAPCs Permit Long-term Expansion of Human Polyclonal CD8+ T Cells

Figure 2A:
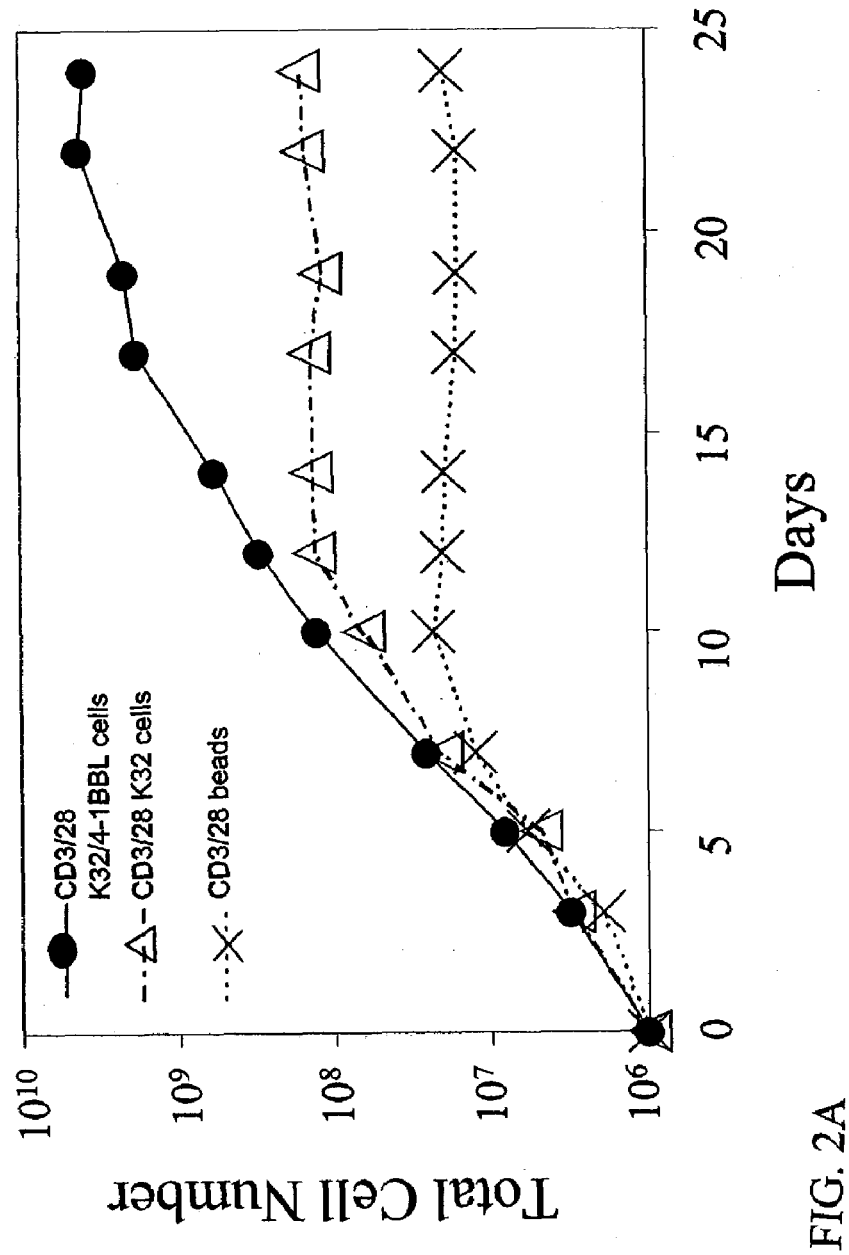
FIGS. 2A-2C depict long-term growth of primary polyclonal human $CD8^+$ T cells stimulated with aAPCs in the absence of exogenous cytokines.

Next, to determine whether the aAPC were sufficient to maintain long term propagation of CD8+ T cells (FIG. 2A). CD8+ T cells were stimulated with aAPCs—but no exogenous cytokines were added to the medium. CD3/28 bead-stimulated cells failed to proliferate after the second stimulation with aAPCs, in agreement with previous findings. Similarly, CD8+ T cells stimulated with CD3/28 in the context of K32 cells entered into a plateau phase of the growth curve within 2 weeks of culture, and no additional net growth of cells occurred after re-stimulation.

In contrast, when CD8+ T cell cultures were stimulated with K32/4-1BBL/CD3/28 aAPCs, they remained in exponential growth even after a third stimulation. This augmentation of long-term proliferation was reproducible, as the average increase in the total number of T cells was 410-fold higher in cultures stimulated with K32/4-1BBL/CD3/28 than in cultures stimulated with CD3/28 beads in six independent experiments.

Figure 2B:
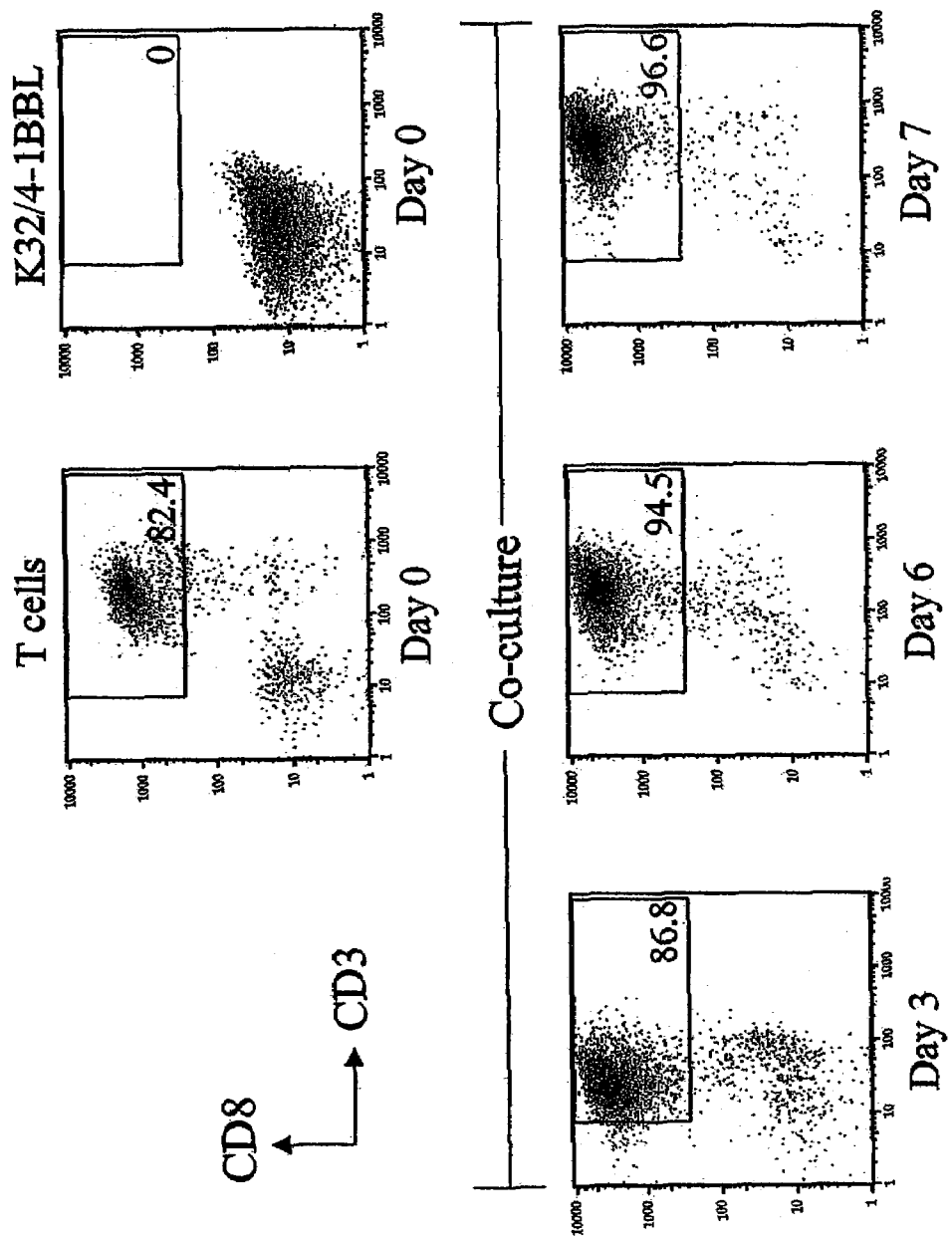
Figure 2C:
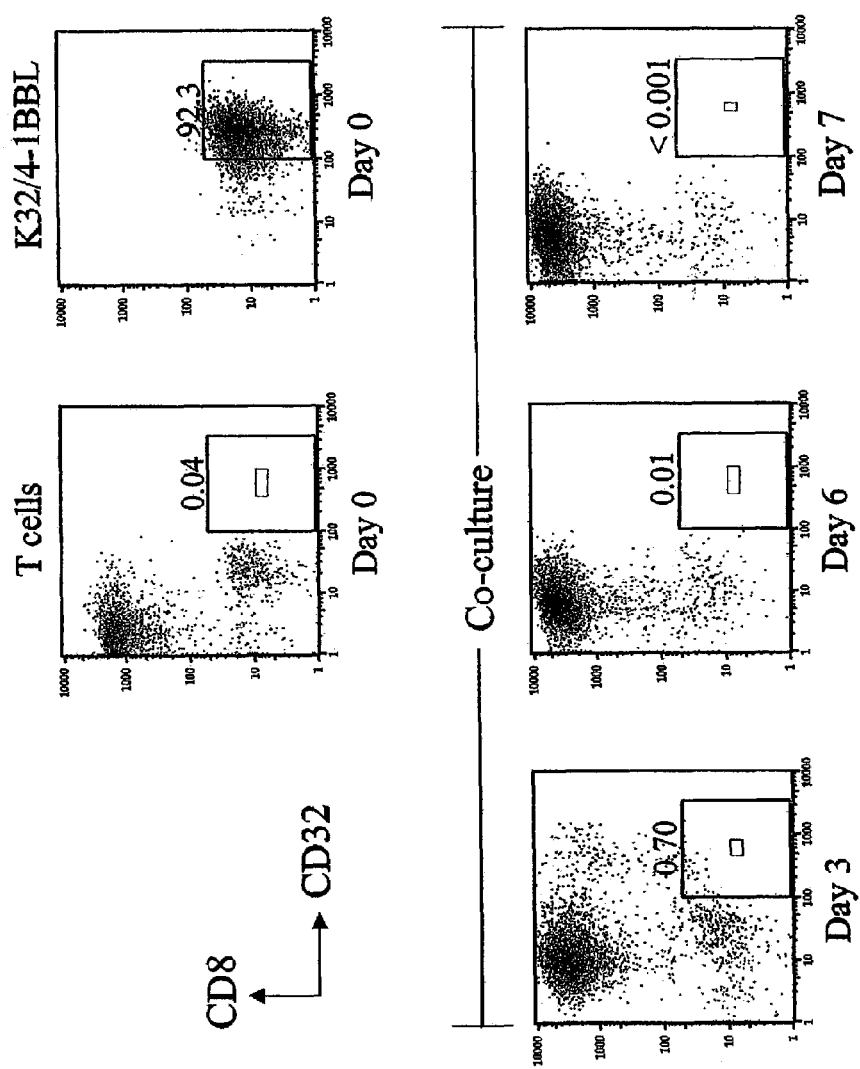

Phenotypic analysis of cultures showed a progressive enrichment for CD3+CD8+ T cells after stimulation with K32/4-1BBL/CD3/28 aAPCs (FIG. 2B). The cell based aAPCs rapidly disappeared from the cell culture, as evidenced by an inability to detect the irradiated K32/4-1BBL cells by flow cytometry after seven days (FIG. 2C). This finding was confirmed in large-scale experiments and also by RT-PCR for CD32 (data not shown). Thus, the mixed T cell and aAPC culture yields a population of essentially pure T cells within one week.

Example 3

Efficient Propagation of Antigen-specific Cytotoxic T Cells by K32/4-1BBL aAPCs

Figure 3A:
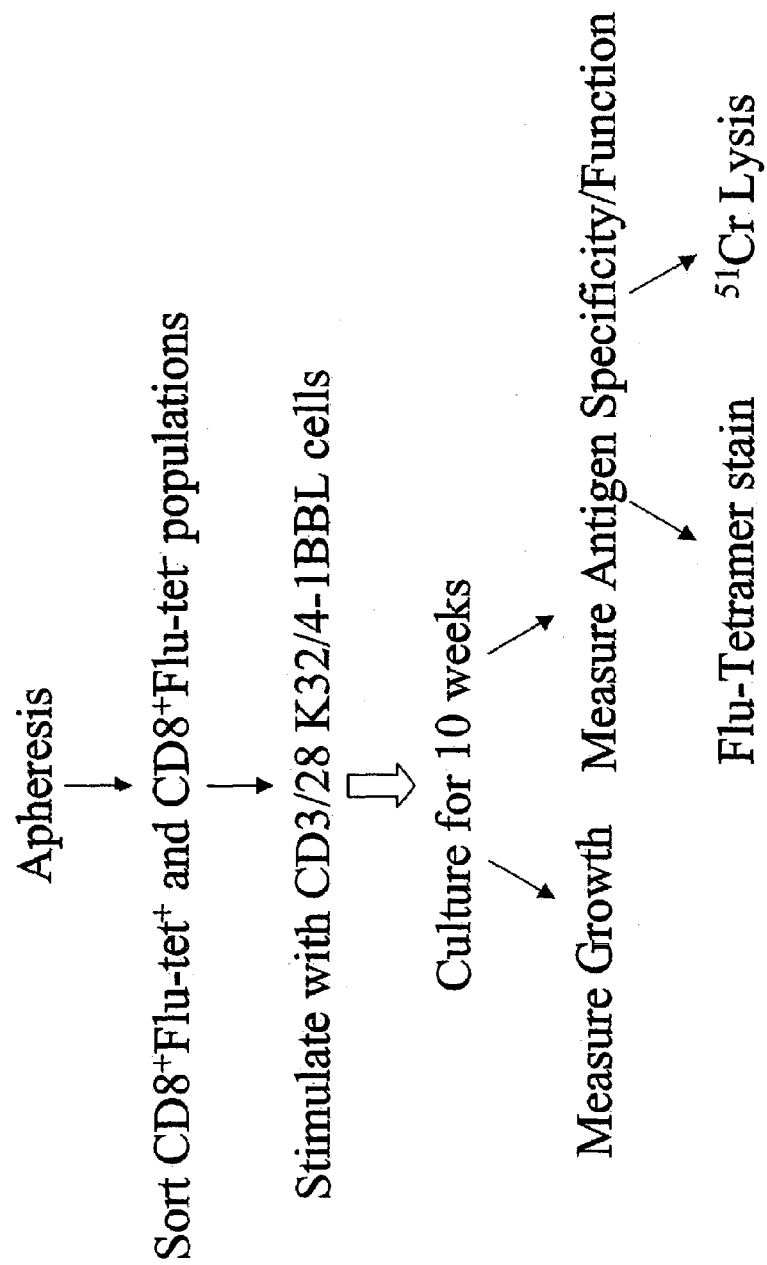
FIGS. 3A-3C depict propagation of antigen-specific cytotoxic T cells from an HLA A*0201 donor using K32/4-1BBL aAPCs.

Because immunotherapy with CD8+ T cells will likely require cells with antigen-specific cytolytic functions, it was necessary to determine whether the K32/4-1BBL aAPCs could be used to expand antigen-specific CTLs, although antigens are not essential in the presentation of the aAPCs. Consequently, they were used to culture a population of MHC tetramer− sorted primary CD8+ T cells for 10 weeks (FIG. 3A). Purified CD8+ T cells obtained from an HLA-A *0201 donor were stained and sorted with an A*0201 MHC tetramer loaded with a flu matrix protein peptide (flu MP tetramer). The tetramer+ population was present at an initial frequency of 0.081% (FIG. 3B), which presumably was composed mainly of memory T cells. Cultures of tetramer−CD8+ T cells served as an internal control population of T cells to assess the growth potential and specificity of the tetramer+ population of CD8+ T cells.

Figure 3B:
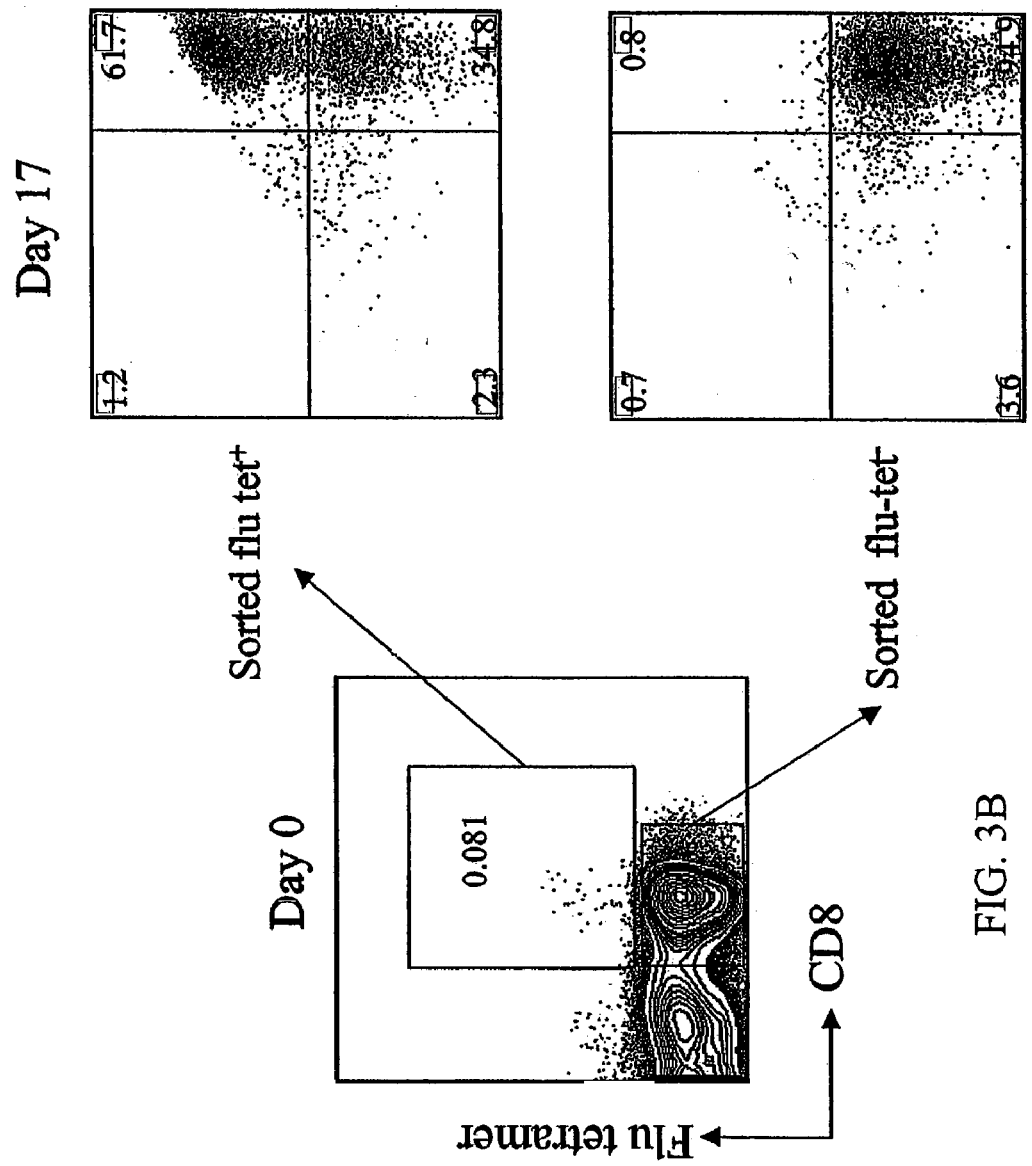
Figure 3C:
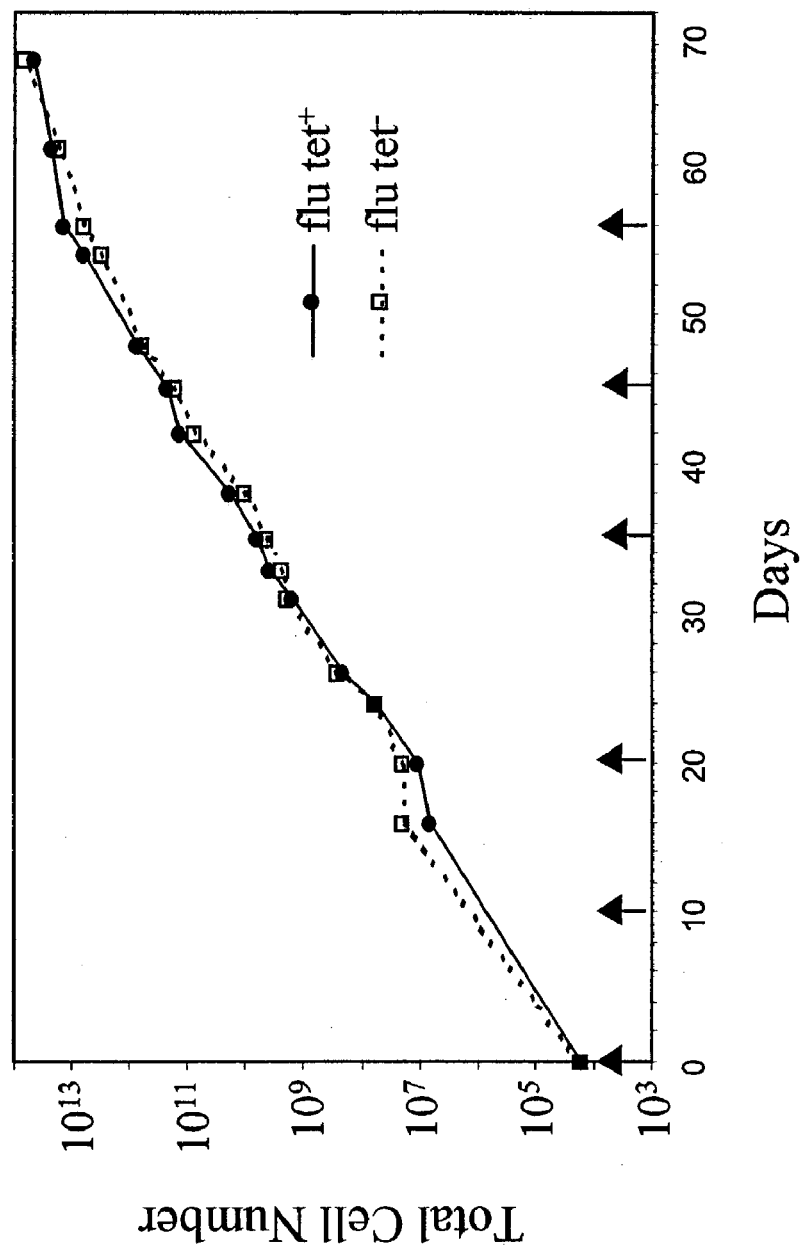

After bulk sorting, 16,000 cells each of CD8+fluMP–tetramer+ and tetramer− phenotype were stimulated with irradiated K32/4-1BBL/CD3/28 aAPCs (FIG. 3C). All cells were re-stimulated with K32/4-1BBL aAPCs at ~10 day intervals and rhIL-2 (20 IU/mL) was added to the culture during the 4th week. No specific flu stimulation was provided during culture. Exponential growth curves of both populations of cells were obtained for several months. The 16,000 antigen-specific T cells yielded $1.5 \times 10^9$ cells after one month of culture, a number of cells sufficient for immunotherapy. The substantial proliferative capacity of the CD8+ T cells that remained after 30 days of culture indicated that these CTLs could have substantial long-term engraftment potential after adoptive transfer.

To determine if antigen specificity of the expanded populations was maintained during culture, cells were stained with flu MP tetramer (FIG. 3B). On day 17, the population that was initially sorted as flu MP tetramer+ was 61.7% CD8+flu MP tetramer+, while the population that was sorted as flu MP tetramer− had negligible staining. The percentage of tetramer+ cells in culture declined somewhat over time, but remained at >20% through day 60 (data not shown).

Similar results were obtained with T cells from another HLA A*0201 donor, where on day 26 of culture, the population sorted as flu MP tetramer+ was 49% CD8+ flu MP tetramer+ and again remained at >20% through day 60 (data not shown). Thus, a single round of selection for CD8+ cells with the desired specificity is sufficient to maintain acceptable purity of CD8+ cells cultured on K32/4-1BBL/CD3/28 aAPCs.

To examine the effector function of the cultured T cells, the antigen-specific cytolytic activity of the flu MP tetramer+ and tetramer− cultures was determined by $^{51}$Cr release assays on days 26, 30, and 56 of ex vivo expansion (data not shown). The HLA-A*0201 TAP deficient T2 cell line, pulsed or unpulsed with the flu MP peptide was used as a target population. At all time points, flu MP tetramer+ cells displayed potent cytotoxicity for flu-MP peptide pulsed targets. Flu MP tetramer+ cells did not kill unpulsed targets, and the Flu MP tetramer cells did not kill either pulsed or unpulsed target cells. Neither effector population killed the parental K562 cells, suggesting that killing was MHC-restricted, and not directed at K562 alloantigens (data not shown). Similar results were obtained with both donors (data not shown).

Example 4

Maintenance of Diverse TCR Repertoire by K32/4-1BBL aAPC.

Given the finding that many tumor antigens are self antigens, adoptive immunotherapy will require the isolation and propagation of T cells with generally low affinity TCRs. Therefore, it is desirable that the culture system propagate T cells with uniform efficiency. To compare the properties of the cultures grown with aAPCs, cultures of CD8+ T cells grown on anti-CD3/28 coated beads, and K32/CD3/28 and K32/4-1BBL/CD3/28 aAPCs were assessed for maintenance of the initial TCR repertoire. CDR3 size length analysis of TCR β-chains was used because it permits sensitive detection of clonal T cell outgrowth.

Figure 4:
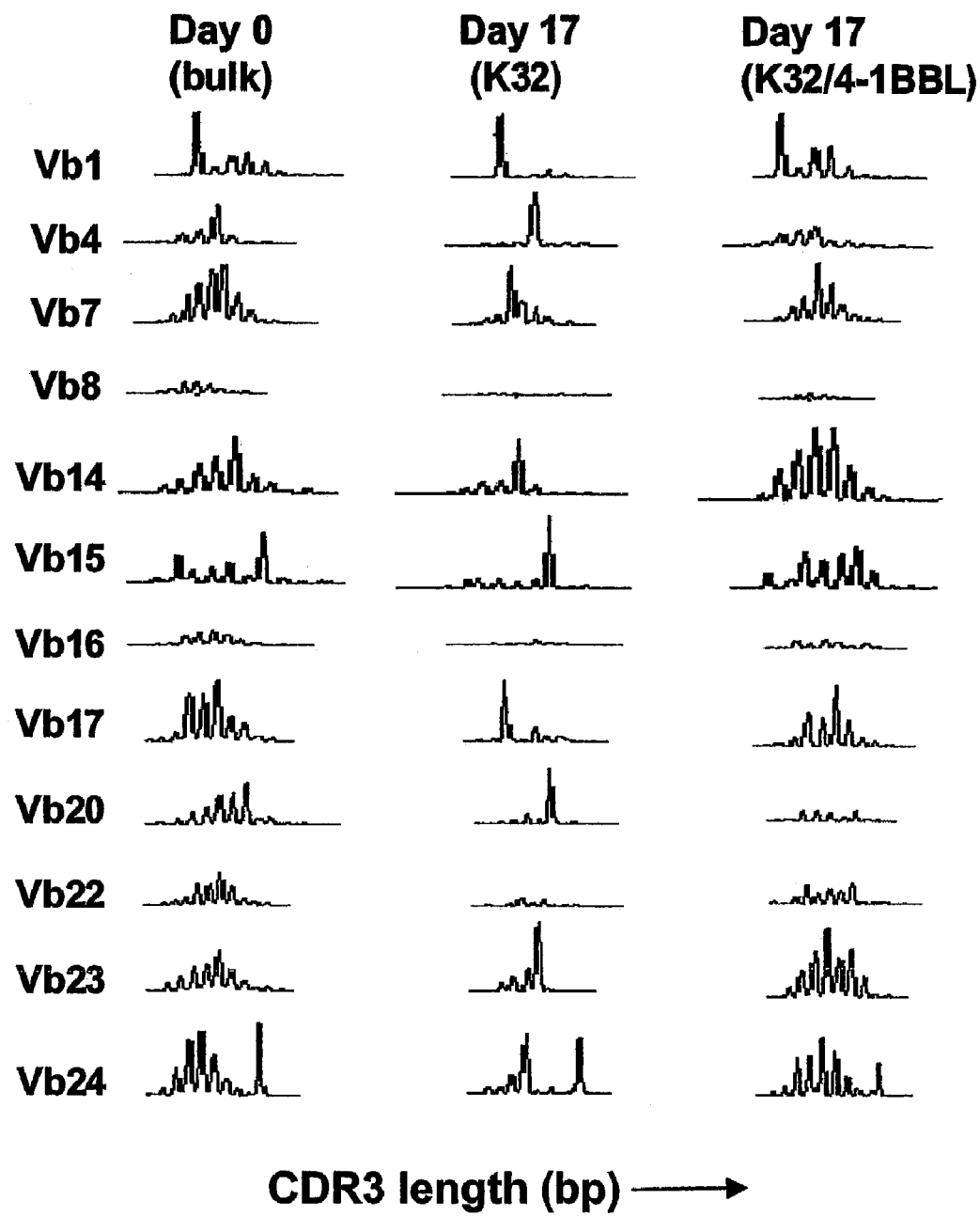
FIG. 4 depicts maintenance of the TCR Vβ repertoire in polyclonal $CD8^+$ T cells after expansion with K32/4-1BBL aAPCs. T cells cultured on K32 or K32/4-1BBL aAPCs from the growth curve shown in FIG. 2 were assessed for the CDR3 length distribution. The indicated TCR Vβ family is shown at baseline, and after 17 days of culture.

It has been previously shown by the inventors that CD3/28 coated beads can maintain diverse CD4+ T cell populations for several months in culture. However, dramatic perturbations of the input CD8 repertoire occurred after two weeks of culture on these beads (data not shown). In contrast, CD8+ T cells cultured on K32/4-1BBL/CD3/28 aAPC maintained CDR3 size length distributions that were similar to the input population of T cells (FIG. 4). The addition of 4-1BBL appeared to account for the preservation of the repertoire, because cultures of CD8+ T cells on K32/CD3/28 aAPC did not maintain a comparably diverse repertoire (FIG. 4).

Example 5

K32/4-1BBL aAPC Stimulation Enhances Survival of Human CD8+ T Cells upon Restimulation.

Because the initial growth rate of CD8+ T cells stimulated with three different aAPCs was similar, it appeared that the increased overall growth observed in K32/4-1BBL/CD3/28 stimulated T cells was due to improved survival. Therefore, a determination was made of the relative effects of the various aAPCs on Bcl-xL and IL-2 expression, two genes involved in T cell survival and proliferation, respectively.

Figure 5A:
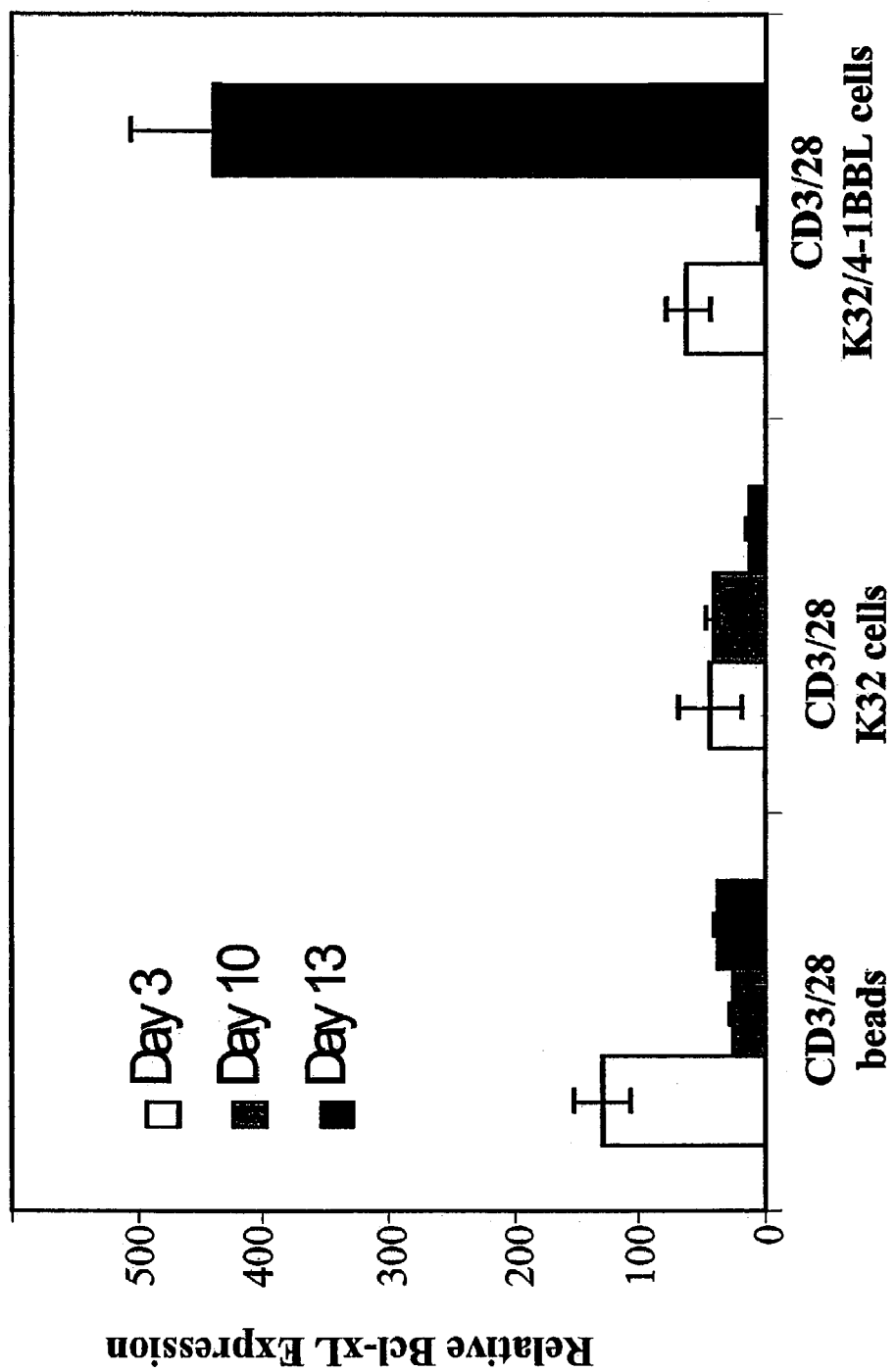
FIGS. 5A and 5B graphically depict expression of genes involved in T-cell growth and survival after stimulation with aAPCs. Real-time quantitative RT-PCR of Bcl-xL (mean±s.e.m.) (FIG. 5A) or IL-2 (FIG. 5B) mRNA in polyclonal $CD8^+$ T cultures. Y-axis: -fold expression of Bcl-xL or IL-2 relative to day 0 of culture. All cultures were stimulated with aAPCs on days 0 and 10. Results are representative of three different experiments with different donors.
Figure 5B:
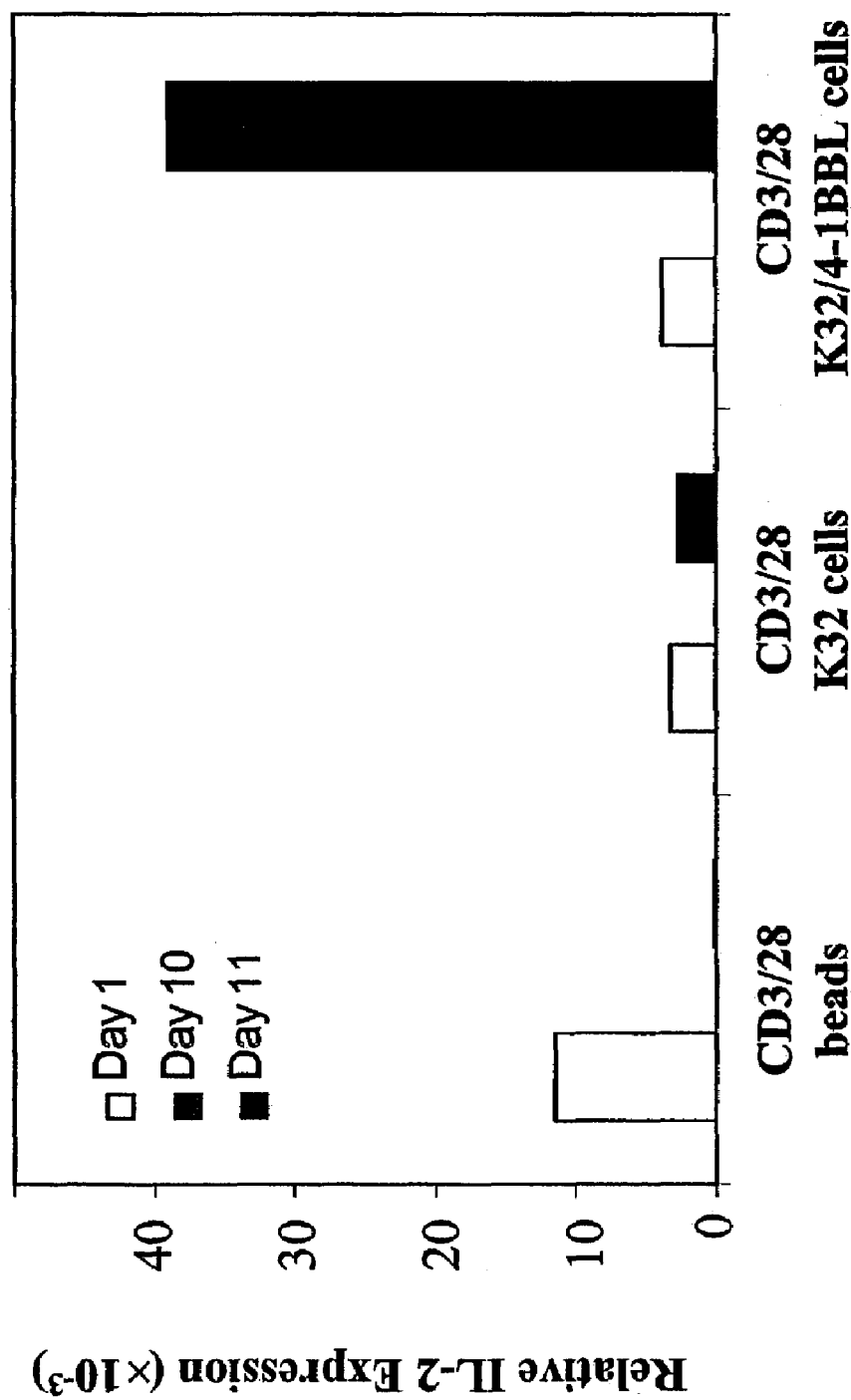

Quantitative real time RT-PCR was used to determine the levels of steady-state mRNA coding for Bcl-xL and IL-2 (FIG. 5). In all cultures, Bcl-xL and IL-2 gene expression was upregulated compared to resting cells one and three days after the first stimulation, and by day 10, Bcl-xL and IL-2 gene expression had returned to resting levels. However, one to three days after re-stimulation, only CD8+ T cell cultures that were stimulated with the K32/4-1BBL/CD3/28 aAPCs had increased levels of Bcl-xL and IL-2 mRNA. In contrast, CD8+ T cells that were stimulated with beads or K32/CD3/28 cells did not re-induce Bcl-xL or IL-2 expression after a second stimulation (FIG. 5A and B, respectively). Together these data suggest that 4-1BB co-stimulation provides a survival signal that is critical for subsequent, but not the initial stimulation, of CD8+ T cell proliferation.

Figure 6:
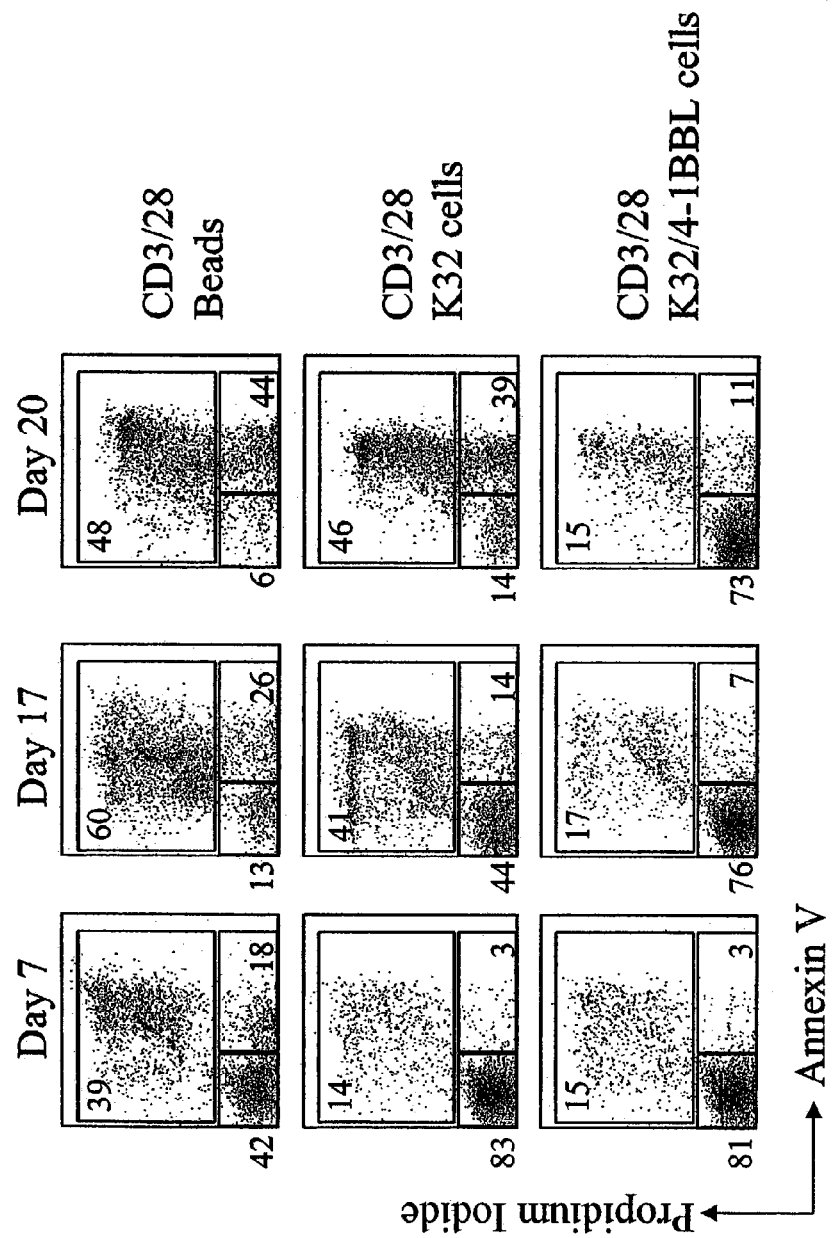
FIG. 6 depicts the distinct effects on apoptosis in cultures of polyclonal human $CD8^+$ T cells stimulated with various aAPCs. Flow-cytometric analysis of cultured cells stained with FITC-labeled annexin V (x-axis) and propidium iodide (y-axis). The three rows represent different aAPCs used for stimulation. The columns represent days in culture. All cultures were stimulated with aAPCs on days 0 and 10. Data shown are not gated. Results are representative of three experiments with different donors.

The viability was assessed of the CD8+ T cells stimulated by the various aAPCs during culture by fluorescent staining with annexin V and propidium iodide (FIG. 6). In the bead-stimulated cultures, viability gradually decreased in the first ten days, and then dropped precipitously as only 6% of cells were viable on day 20. In the T cell cultures stimulated with K32 aAPCs, T cell viability seven days after the second stimulation was improved compared to bead-stimulated cells. However, most of the cells died by day 20.

In contrast, K32/4-1BBL/CD3/28 stimulated CD8+ T cell cultures were >70% viable throughout culture. Together these results show that the addition of 4-1BBL co-stimulation prevents apoptosis and preserves the starting repertoire of CD8+ T cells.

In sum, the K562 cell based aAPC system is able to maintain long term exponential growth of viable T cells, particularly CD8+ memory cells for many months in vitro. Based on a starting cell population of $10^4$ influenza specific CD8+ T cells, a sufficient number of CTL were obtained for therapy after only 30 days of culture. Since the starting number of antigen specific CD8+ T cells could be isolated from only 100 ml of blood, given an initial frequency of 0.05%, it would be possible to decrease the culture time to only two weeks by performing a lymphopheresis and isolating $10^5$ to $10^6$ antigen-specific CD8+ T cells. High speed cell sorting or magnetic bead separation can isolate sufficient CD8+ memory cells for initial culture on K32/4-1BBL aAPC coated with anti-CD3 and CD28 antibodies. Alternatively, it is possible to coat the K32/4-1BBL aAPC with the desired tetramer in order to culture antigen specific T cells de novo, and obviate the need for a separate cell isolation procedure. The flexibility of the present system is particularly advantageous, in that the engineering of the aAPC can be modified and focussed based upon the specific T cell need.

One implication of the present system is that the CTLs retain a substantial replicative capacity after culture with the K32/4-1BBL/CD3/28 aAPCs, even after reaching therapeutic numbers for clinical infusion. Several mechanisms appear to account for the improved growth and repertoire of K32/4-1BBL/CD3/28 stimulated CD8+ T cells. For instance, as noted, there was a markedly improved survival of CD8+ T cells after repeated stimulation with K32/4-1BBL/CD3/28 aAPC, as compared with CD3/28 coated beads. With the addition of 4-1BB co-stimulation, CD8+ T cells have increased expression of IL-2 and Bcl-xL, improved survival, and continued proliferation after re-stimulation with anti-CD3/CD28. Thus, 4-1BB stimulation in this context overcomes the previously described activation-induced non-responsiveness.

Not all clinically useful antigens are presently characterized as MHC-restricted epitopes, and the library of MHC tetramers for many HLA types remains limiting. Therefore, K32/4-1BBL/CD3/28 aAPCs were also used to expand CTLs that have been previously enriched for a particular antigen-specificity by priming with autologous DC that have been pulsed with apoptotic bodies of autologous tumor (unpublished data). Thus, K32/4-1BBL/CD3/28 aAPCs are likely to be complementary to many methods, including MHC tetramer sorting (Dunbar et al., Curr. Biol. 8:413-416 (1998); Yee, et al., J. Immunol. 162:2227-2234 (1999)), or priming with autologous DCs or other artificial APCs (Latouche et al., 2000), that enrich for antigen-specific CTL populations. Although thus far the K32/4-1BBL/CD3/28 aAPCs have been tested for their ability to expand memory or primed T cells; they and other APC constructs will be useful to expand naive CD8+ cells as a source of the 'self' repertoire for tumor immunotherapy (Curtsinger et al., J. Immunol. 160:3236-3243 (1998); Sagerstrom et al., Proc. Natl. Acad. Sci. USA 90:8987-8991 (1993); Wang et al., J. Immunol. 164:1216-1222 (2000).

Expanding low-avidity, self-reactive T cells Voltz et al., N. Engl. J. Med. 340:1788-1795 (1999) that can differentiate into memory cells (Tan, J. Clin. Invest. 108:1411-1415 (2001)) offers a useful approach to derive therapeutic numbers of self reactive CTLs. Advantageously, because only T cells that recognize the MHC/peptide complex are activated in the present invention, rapid expansion is provided for selected antigen specific clones. Once characterized, these cell lines will be invaluable tools for immunotherapy, particularly since the cell lines permit the design of optimal co-stimulation regimes on a disease-by-disease basis. Moreover, given that GMP preparations of anti-CD3 and CD28 antibodies are currently available, and that K32/4-1BBL aAPC can be grown in serum free medium, the system of the present invention provides therapeutic resources for clinical adoptive immunotherapy for patients with cancer and viral diseases, as well as for the in vitro propagation of CTLs for experimentation. Finally, in light of the many co-stimulatory molecules that continue to be discovered, e.g., OX40L, CD40, CD80, CD86, GL50, 4-1BBL and B7-H1, that serve to either augment the level of T cell growth or alter the functional ability of the T cells, the present invention offers novel methods by which the usefulness of these additional co-stimulators can be evaluated as immunotherapeutic agents by transfecting them into K-32 cells and testing their effect on overall T cell growth and in functional assays.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A method for inducing a population of T cells to rapidly proliferate exponentially, the method comprising stimulating T cells by contacting the T cells ex vivo with an engineered K562 cell, wherein said engineered K562 cell comprises on its surface: an anti-CD3 antibody loaded onto a human Fcγ receptor, wherein said human Fcγ receptor is expressed from an expression vector in said engineered K562 cell; a ligand for CD28 selected from the group consisting of anti-CD28 antibody, CD80, and CD86; and 4-1BBL, thereby inducing the T cells to rapidly proliferate exponentially, wherein said engineered K562 cell permits long term expansion of T cells.

2. The method of claim 1, wherein the anti-CD3 antibody and the anti-CD28 antibody are human antibodies.

3. The method of claim 1, wherein said 4-1BBL is of human origin.

4. The method of claim 1, further comprising monitoring exponential proliferation of the T cells in response to continuing exposure to the ligand; and re-activating and re-stimulating the T cells when the rate of T cell proliferation has decreased, thereby inducing further proliferation of the T cells.

5. The method of claim 1, further comprising repeating the steps of stimulating to produce a population of T cells increased in number from about 100- to about 100,000-fold the original T cell population.

6. The method of claim 1, wherein the T cells comprise $CD4^+$ T cells or $CD8^+$ T cells, or a combination thereof.

7. A method for stimulating a population of $CD8^+$ T cells to rapidly proliferate exponentially for a long term, the method comprising stimulating and restimulating CD8+ T cells by contacting the $CD8^+$ T cells ex vivo with an engineered K562 cell, wherein said engineered K562 cell comprises on its surface: an anti-CD3 antibody loaded onto a human Fcγ receptor, wherein said human Fcγ receptor is expressed from an expression vector in said engineered K562 cell, a ligand for CD28 selected from the group consisting of anti-CD28 antibody, CD80, and CD86; and 4-1BBL thereby stimulating the T cells to rapidly proliferate exponentially for a long term.

8. The method of claim 7, wherein said anti-CD3 antibody, anti-CD28 antibody and 4-1BBL are human.

9. A method of inducing a population of T cells from a subject to rapidly proliferate exponentially comprising:
    a) isolating a population of T cells from a subject; and
    b) stimulating T cells by contacting the T cells ex vivo with at least an engineered K562 cell, wherein said engineered K562 cell comprises on its surface: an anti-CD3 antibody loaded onto a human Fcγ receptor, wherein said human Fcγ receptor is expressed from an expression vector in said engineered k562 cell, a ligand for CD28 selected from the group consisting of anti-CD28 antibody, CD80, and CD86; and 4-1BBL; thereby inducing the T cells to rapidly proliferate exponentially.

10. The method of claim 9, wherein the subject is human.

11. The method of claim 10, wherein the subject is infected with a disease or condition.

12. The method of claim 11, wherein the disease or condition is cancer.

13. The method of claim 11, wherein the disease or condition is autoimmune disorder.

14. The method of claim 11, wherein the disease or condition is associated with an infectious disease or pathogen.

15. The method of claim 1, further comprising restimulating said T cells, wherein said restimulation comprises contacting said T cells with said engineered K562 cell.

* * * * *